United States Patent
Ou et al.

(10) Patent No.: US 11,666,614 B2
(45) Date of Patent: Jun. 6, 2023

(54) PROBIOTIC BACTERIA ISOLATED FROM WOLVES AND RELATED COMPOSITIONS AND METHODS

(71) Applicant: CanBiocin Inc., Edmonton (CA)

(72) Inventors: Qixing Ou, Edmonton (CA); John F. Burlet, Edmonton (CA)

(73) Assignee: CanBiocin Inc., Edmonton (CA)

( * ) Notice: Subject to any disclaimer, the term of this patent is extended or adjusted under 35 U.S.C. 154(b) by 0 days.

(21) Appl. No.: 17/269,885

(22) PCT Filed: Aug. 21, 2019

(86) PCT No.: PCT/CA2019/051140
§ 371 (c)(1),
(2) Date: Feb. 19, 2021

(87) PCT Pub. No.: WO2020/037414
PCT Pub. Date: Feb. 27, 2020

(65) Prior Publication Data
US 2021/0315949 A1 Oct. 14, 2021

Related U.S. Application Data

(60) Provisional application No. 62/720,180, filed on Aug. 21, 2018.

(51) Int. Cl.
| | | |
|---|---|---|
| *A61K 35/747* | (2015.01) | |
| *C12N 1/20* | (2006.01) | |
| *A23K 50/40* | (2016.01) | |
| *A23K 10/18* | (2016.01) | |
| *C12R 1/25* | (2006.01) | |
| *C12R 1/46* | (2006.01) | |
| *C12R 1/24* | (2006.01) | |

(52) U.S. Cl.
CPC ............ *A61K 35/747* (2013.01); *A23K 10/18* (2016.05); *A23K 50/40* (2016.05); *C12N 1/205* (2021.05); *C12R 2001/24* (2021.05); *C12R 2001/25* (2021.05); *C12R 2001/46* (2021.05)

(58) Field of Classification Search
None
See application file for complete search history.

(56) References Cited

U.S. PATENT DOCUMENTS 9,095,160 B2 * 8/2015 Beasley ................. A23K 50/40

FOREIGN PATENT DOCUMENTS

| CA | 2 890 965 A1 | 11/2015 |
|---|---|---|
| EP | 3 318 625 A2 | 5/2018 |

OTHER PUBLICATIONS

Lyu et al. AMB Express, 2018, 8; 123, pp. 1-12; published on Aug. 2, 2018.*
Written Opinion of the International Searching Authority dated Oct. 24, 2019, issued in corresponding Application No. PCT/CA2019/051140, filed Aug. 21, 2019, 5 pages.
International Search report dated Oct. 24, 2019, issued in corresponding Application No. PCT/CA2019/051140, filed Aug. 21, 2019, 3 pages.
Pallin, A., "Lactobacilli in the gastrointestinal tract of dog and wolf: Isolation, identification and characterization of *L. reuteri*," master's thesis, Swedish University of Agricultural Sciences: Department of Microbiology, Uppsala, Sweden, 2012, pp. 5-44.
Extended European Search Report dated Jan. 4, 2022, issued in corresponding European Patent Application No. 19852107.2, filed Aug. 21, 2019, 10 pages.
Beasley et al., "Lactic acid bacteria isolated from canine faeces", Journal of Applied Microbiology, 2006, pp. 131, 138.
Shave et al., "Seasonal and inter-annual variation in diet for gray wolves *Canis lupus* in Prince Albert National Park", , BioOne Complete, Wildlife Biology, Jun. 23, 2020, 10 pages.

* cited by examiner

*Primary Examiner* — Vera Afremova
(74) *Attorney, Agent, or Firm* — Christensen O'Connor Johnson Kindness PLLC

(57) ABSTRACT

Isolates strains of gastrointestinal bacteria from wolves are provided for use as probiotics. In some embodiments, the isolated strains are for use as probiotics in canine subjects such as domestic dogs. In some embodiments, the isolated strains may be used to treat or prevent intestinal dysbiosis in the subject. Also provided are compositions comprising at least one isolated strain of wolf probiotic bacteria and related methods for making same.

13 Claims, 16 Drawing Sheets

Specification includes a Sequence Listing.

*Lactobacillus reuteri* WF-1
SEQ ID NO: 1
Saskatoon 20170323; 16S rDNA

AGCGTCAGTTGCAGACCAGACAGCCGCCTTCGCCACTGGTGTTCTTCCATATATCTA
CGCATTCCACCGCTACACATGGAGTTCCACTGTCCTCTTCTGCACTCAAGTCGCCCG
GTTTCCGATGCACTTCTTCGGTTAAGCCGAAGGCTTTCACATCAGACCTAAGCAACC
GCCTGCGCTCGCTTTACGCCCAATAAATCCGGATAACGCTTGCCACCTACGTATTAC
CGCGGCTGCTGGCACGTAGTTAGCCGTGACTTTCTGGTTGGATACCGTCACTGCGTG
AACAGTTACTCTCACGCACGTTCTTCTCCAACAACAGAGCTTTACGAGCCGAAACCC
TTCTTCACTCACGCGGTGTTGCTCCATCAGGCTTGCGCCCATTGTGGAAGATTCCCTA
CTGCTGCCTCCCGTAGGAGTATGGACCGTGTCTCAGTTCCATTGTGGCCGATCAGNC
TCTCAACTCGGCTATGCATCATCGCCTTGGTAAGCCGTTACCTTACCAACTAGCTAAT
GCACCGCAGGTCCATCCCAGAGTGATAGCCAAAGCCATCTTTCAARCAAAAGCCAT
GTGGCTTTTGTTGTTATGCGGTATTAGCATCTGTTTCCAAATGTTATCCCCCGCTCCG
GGGCAGGTTACCTACGTGTTACTCACCCGTCCGCCACTCACTGGTGATCCATCGTCA
ATCAGGTGCAAGCACCATCAATCAGTTGGGCCAGTGCGTACGACTTGCATGTATTAG
GCACACCGCCGGCGTTCATCCTGA

Fig. 2A

*Lactobacillus animalis* WF-2
SEQ ID NO: 2
Saskatoon 20170323; 16S rDNA

TTACAGACCAGAGAGCCGCTTTCGCCACTGGTGTTCTTCCATATATCTACGCATTTCA
CCGCTACACATGGAGTTCCACTCTCCTCTTCTGCACTCAAGTCTCCCAGTTTCCAATG
CACTACTCCGGTTAAGCCGAAGGCTTTCACATCAGACTTAAAAGACCGCCTGCGTTC
CCTTTACGCCCAATAAATCCGGATAACGCTTGCCACCTACGTATTACCGCGGCTGCT
GGCACGTAGTTAGCCGTGGCTTTCTGGTTAGATACCGTCGAAACGTGAACAGTTACT
CTCACGCACTTTCTTCTCTAACAACAGGGTTTTACGATCCGAAGACCTTCTTCACCCA
CGCGGCGTTGCTCCATCAGGCTTTCGCCCATTGTGGAAGATTCCCTACTGCTGCCTCC
CGTAGGAGTTTGGGCCGTGTCTCAGTCCCAATGTGGCCGATCAACCTCTCAGTTCGG
CTACGCATCATTGCCTTGGTAAGCCTTTACCTCACCAACTAGCTAATGCGCCGCGGG
CCCATCCAAAAGCGGTAGCATAGCCACCTTTTACATAGTTACCATGCGGTAACTATG
GTTATGCGGTATTAGCACCTGTTTCCAAGTGTTATCCCCCTCTTTGGGCAGGTTGCC
CACGTGTTACTCACCCGTTCGCCACTCAACTCTTTATCGGTGAGTGCAAGCACTCGG
TGA

Fig. 2B

*Enterococcus faecium* WF-3
SEQ ID NO: 3
Saskatoon 20170906; 16S rDNA

AGCCGCCTTCGCCACTGGTGTTCCTCCATATATCTACGCATTTCACCGCTACACATGG
AATTCCACTCTCCTCTTCTGCACTCAAGTCTCCCAGTTTCCAATGACCCTCCCCGGTT
GAGCCGGGGGCTTTCACATCAGACTTAAGAAACCGCCTGCGCTCGCTTTACGCCCAA
TAAATCCGGACAACGCTTGCCACCTACGTATTACCGCGGCTGCTGGCACGTAGTTAG
CCGTGGCTTTCTGGTTAGATACCGTCAAGGGATGAACAGTTACTCTCATCCTTGTTCT
TCTCTAACAACAGAGTTTTACGATCCGAAAACCTTCTTCACTCACGCGGCGTTGCTC
GGTCAGACTTTCGTCCATTGCCGAAGATTCCCTACTGCTGCCTCCCGTAGGAGTTTG
GGCCGTGTCTCAGTCCCAATGTGGCCGATCACCCTCTCAGGTCGGCTATGCATCGTG
GCCTTGGTGAGCCGTTACCTCACCAACTAGCTAATGCACCGCGGGTCCATCCATCAG
CGACACCCGAAAGCGCCTTTCAAATCAAAACCATGCGGTTTNGATTGTTATACGGTA
TTAGCACCTGTTTCCAAGTGTTATCCCCTTCTGATGGGCAGGTTACCCACGTGTTACT
CACCCGTTCGCCACTCCTCTTTTTCCGGTGGAGCAAGCTCCGGTGGAAAAAGAAGCG
TTCGACTTGCATGTATTA

Fig. 2C

*Lactobacillus plantarum* WF-4
SEQ ID NO: 4
Saskatoon 20170906; 16S rDNA

AGCGTCAGTTACAGACCAGACAGCCGCCTTCGCCACTGGTGTTCTTCCATATATCTA
CGCATTTCACCGCTACACATGGAGTTCCACTGTCCTCTTCTGCACTCAAGTYTCCCAG
TTTCCGATGCACTTCTTCGGTTGAGCCGAANGCTTTCACATCAGACTTAAAAAACCG
CCTGCGCTCGCTTTACGCCCAATAAATCCGGACAACGCTTGCCACCTACGTATTACC
GCGGCTGCTGGCACGTAGTTAGCCGTGGCTTTCTGGTTAAATACCGTCAATACCTGA
ACAGTTACTCTCAGATATGTTCTTCTTTAACAACAGAGTTTTACGAGCCGAAACCCTT
CTTCACTCACGCGGCGTTGCTCCATCAGACTTTCGTCCATTGTGGAAGATTCCCTACT
GCTGCCTCCCGTAGGAGTTTGGGCCGTGTCTCAGTCCCAATGTGGCCGATTACCCTC
TCAGGTCGGCTACGTATCATTGCCATGGTGAGCCGTTACCCCACCATCTAGCTAATA
CGCCGCGGGACCATCCAAAAGTGATAGCCGAAGCCATCTTTCAANCTCGGACCATG
CGGTCCAAGTTGTTATGCGGTATTAGCATCTGTTTCCAGGTGTTATCCCCCGCTTCTG
GGCAGGTTTCCCACGTGTTACTCACCAGTTCGCCACTCACTCAAATGTAAATCATGA
TGCAAGCACCAATCAATACCAGAGTTCGTTCGACTTGCATGTATTANGCACGCCGCC
AGCGTTCGTCCTGAGC

Fig. 2D

*Lactobacillus brevis* WF-5
SEQ ID NO: 5
Saskatoon 20170906; 16S rDNA

ACAGCCGCCTTCGCCACTGGTGTTCTTCCATATATCTACGCATTCCACCGCTACACAT
GGAGTTCCACTGTCCTCTTCTGCACTCAAGTCTCCCAGTTTCCGATGCACTTCTCCGG
TTAAGCCGAAGGCTTTCACATCAGACTTAAAAAACCGCCTGCGCTCGCTTTACGCCC
AATAAATCCGGACAACGCTTGCCACCTACGTATTACCGCGGCTGCTGGCACGTAGTT
AGCCGTGGCTTTCTGGTTAAATACCGTCAACCCTTGAACAGTTACTCTCAAAGGTGT
TCTTCTTTAACAACAGAGTTTTACGAGCCGAAACCCTTCTTCACTCACGCGGCATTGC
TCCATCAGACTTTCGTCCATTGTGGAAGATTCCCTACTGCTGCCTCCCGTAGGAGTTT
GGGCCGTGTCTCAGTCCCAATGTGGCCGATTACCCTCTCAGGTCGGCTACGTATCAT
CGTCTTGGTGGGCCTTTACCTCACCAACTAACTAATACGCCGCGGGATCATCCAGAA
GTGATAGCCGAAGCCACCTTTCAAACAAAATCCATGCGGATTNTGTTGTTATACGGT
ATTAGCACCTGTTTCCAAGTGTTATCCCCTGCTTCTGGGCAGATTTCCCACGTGTTAC
TCACCAGTTCGCCACTCGCTTCATTGTTGAAATCAGTGCAAGCACGTCATTCAACGG
AAGCTCGTTCGACTTGCATGTATTANGCATGCCGCCAGCGTTCGTCCTGA

Fig. 2E

*Lactobacillus curvatus* WF-6
SEQ ID NO: 6
Saskatoon 20170906; 16S rDNA

GCGTCAGTTACAGACCAGACAGCCGCCTTCGCCACTGGTGTTCTTCCATATATCTAC
GCATTTCACCGCTACACATGGAGTTCCACTGTCCTCTTCTGCACTCAAGTTTCCCAGT
TTCCGATGCACTTCTTCGGTTGAGCCGAAGGCTTTCACATCAGACTTAAGAAACCGC
CTGCGCTCGCTTTACGCCCAATAAATCCGGACAACGCTTGCCACCTACGTATTACCG
CGGCTGCTGGCACGTAGTTAGCCGTGGCTTTCTGGTTGGATACCGTCACTACCTGAT
CAGTTACTATCAAATACGTTCTTCTCCAACAACAGAGTTTTACGATCCGAAAACCTT
CTTCACTCACGCGGCGTTGCTCCATCAGACTTTCGTCCATTGTGGAAGATTCCCTACT
GCTGCCTCCCGTAGGAGTCTGGGCCGTGTCTCAGTCCCAGTGTGGCCGATTACCCTC
TCAGGTCGGCTATGCATCACGGTCTTGGTGAGCCTTTACCTCACCAACTAACTAATG
CACCGCGGGTCCATCCTAAAGTGATAGCCGAAACCATCTTTCAACCTTGCACCATGC
GGTGCTAGGTTTTATGCGGTATTAGCATCTGTTTCCAAATGTTATCCCCACTTTAGG
GCAGGTTACCCACGTGTTACTCACCCGTCCGCCACTCACTCAAATGTTATCAATCAG
AAGCAAGCTTCTTCAATCTAACGAGAGTGCGTTCGACTTGCATGTATTANGCACGCC
GCCAGCGTTCGTCCTGAGCCA

Fig. 2F

*Lactobacillus reuteri* WF-7
SEQ ID NO: 7
Saskatoon 20170906; 16S rDNA

AGCGTCAGTTGCAGACCAGACAGCCGCCTTCGCCACTGGTGTTCTTCCATATATCTA
CGCATTCCACCGCTACACATGGAGTTCCACTGTCCTCTTCTGCACTCAAGTCGCCCG
GTTTCCGATGCACTTCTTCGGTTAAGCCGAAGGCTTTCACATCAGACCTAANCAACC
GCCTGCGCTCGCTTTACGCCCAATAAATCCGGATAACGCTTGCCACCTACGTATTAC
CGCGGCTGCTGGCACGTAGTTAGCCGTGACTTTCTGGTTGGATACCGTCACTGCGTG
AACAGTTACTCTCACGCACGTTCTTCTCCAACAACAGAGCTTTACGAGCCGAAACCC
TTCTTCACTCACGCGGTGTTGCTCCATCAGGCTTGCGCCCATTGTGGAAGATTCCCTA
CTGCTGCCTCCCGTAGGAGTATGGACCGTGTCTCAGTTCCATTGTGGCCGATCAGNC
TCTCAACTCGGCTATGCATCATCGCCTTGGTAAGCCGTTACCTTACCAACTAGCTAAT
GCACCGCAGGTCCATCCCAGAGTGATAGCCAAAGCCATCTTTCAANCAAAAGCCAT
GTGGCTTTTGTTGTTATGCGGTATTAGCATCTGTTTCCAAATGTTATCCCCCGCTCCG
GGGCANGTTACCTACGTGTTACTCACCCGTCCGCCACTCACTGGTGATCCATCGTCA
ATCAGGTGCAAGCACCATCAATCAGTTGGGCCAGTGCGTACNACTTGCATGTATTAG
GCACACCGCCGGCGTTCATCCTGA

Fig. 2G

SEQUENCE LISTING

```
<160> NUMBER OF SEQ ID NOS: 28

<210> SEQ ID NO 1
<211> LENGTH: 767
<212> TYPE: DNA
<213> ORGANISM: Lactobacillus reuteri
<220> FEATURE:
<221> NAME/KEY: misc_feature
<222> LOCATION: (456)..(456)
<223> OTHER INFORMATION: n is a, t, g, or c
<220> FEATURE:
<221> NAME/KEY: misc_feature
<222> LOCATION: (561)..(561)
<223> OTHER INFORMATION: r is a or g
```

```
<400> SEQUENCE: 1
agcgtcagtt gcagaccaga cagccgcctt cgccactggt gttcttccat atatctacgc      60
attccaccgc tacacatgga gttccactgt cctcttctgc actcaagtcg cccggtttcc     120
gatgcacttc ttcggttaag ccgaaggctt tcacatcaga cctaagcaac cgcctgcgct     180
cgctttacgc ccaataaatc cggataacgc ttgccaccta cgtattaccg cggctgctgg     240
cacgtagtta gccgtgactt tctggttgga taccgtcact gcgtgaacag ttactctcac     300
gcacgttctt ctccaacaac agagcttac gagccgaaac ccttcttcac tcacgcggtg      360
ttgctccatc aggcttgcgc ccattgtgga agattccta ctgctgcctc ccgtaggagt      420
atggaccgtg tctcagttcc attgtggccg atcagnctct caactcggct atgcatcatc     480
gccttggtaa gccgttacct taccaactag ctaatgcacc gcaggtccat cccagagtga     540
tagccaaagc catctttcaa rcaaaagcca tgtggctttt gttgttatgc ggtattagca     600
tctgtttcca aatgttatcc cccgctccgg ggcaggttac ctacgtgtta ctcacccgtc     660
cgccactcac tggtgatcca tcgtcaatca ggtgcaagca ccatcaatca gttgggccag     720
tgcgtacgac ttgcatgtat taggcacacc gccggcgttc atcctga                   767

<210> SEQ ID NO 2
<211> LENGTH: 692
<212> TYPE: DNA
<213> ORGANISM: Lactobacillus animalis

<400> SEQUENCE: 2
ttacagacca gagagccgct ttcgccactg gtgttcttcc atatatctac gcatttcacc      60
gctacacatg gagttccact ctcctcttct gcactcaagt ctcccagttt ccaatgcact     120
actccggtta agccgaaggc tttcacatca gacttaaaag accgcctgcg ttcccttac      180 gcccaataaa tccggataac gcttgccacc tacgtattac gcggctgct ggcacgtagt      240 tagccgtggc tttctggtta gataccgtcg aaacgtgaac agttactctc acgcactttc     300
ttctctaaca acagggtttt acgatccgaa gaccttcttc acccacgcgg cgttgctcca     360
tcaggctttc gcccattgtg gaagattccc tactgctgcc tcccgtagga gtttgggccg     420
tgtctcagtc ccaatgtggc cgatcaacct ctcagttcgg ctacgcatca ttgccttggt     480 aagccttttac ctcaccaact agctaatgcg ccgcgggccc atccaaaagc ggtagcatag     540 ccaccttta catagttacc atgcggtaac tatggttatg cggtattagc acctgtttcc     600
aagtgttatc ccctcttttt gggcaggttg cccacgtgtt actcacccgt tcgccactca     660
actctttatc ggtgagtgca agcactcggt ga                                   692

<210> SEQ ID NO 3
<211> LENGTH: 706
<212> TYPE: DNA
<213> ORGANISM: Enterococcus faecium
<220> FEATURE:
<221> NAME/KEY: misc_feature
<222> LOCATION: (558)..(558)
<223> OTHER INFORMATION: n is a, t, g, or c

<400> SEQUENCE: 3
agccgccttc gccactggtg ttcctccata tatctacgca tttcaccgct acacatggaa      60
ttccactctc ctcttctgca ctcaagtctc ccagtttcca atgaccctcc ccggttgagc     120
cgggggcttt cacatcagac ttaagaaacc gcctgcgctc gctttacgcc caataaatcc     180
ggacaacgct tgccacctac gtattaccgc ggctgctggc acgtagttag ccgtggcttt     240
```

| | |
|---|---|
| ctggttagat accgtcaagg gatgaacagt tactctcatc cttgttcttc tctaacaaca | 300 |
| gagttttacg atccgaaaac cttcttcact cacgcggcgt tgctcggtca gactttcgtc | 360 |
| cattgccgaa gattccctac tgctgcctcc cgtaggagtt tgggccgtgt ctcagtccca | 420 |
| atgtggccga tcaccctctc aggtcggcta tgcatcgtgg ccttggtgag ccgttacctc | 480 |
| accaactagc taatgcaccg cgggtccatc catcagcgac acccgaaagc gcctttcaaa | 540 |
| tcaaaaccat gcggtttnga ttgttatacg gtattagcac ctgtttccaa gtgttatccc | 600 |
| cttctgatgg gcaggttacc cacgtgttac tcacccgttc gccactcctc tttttccggt | 660 |
| ggagcaagct ccggtggaaa agaagcgtt cgacttgcat gtatta | 706 |

```
<210> SEQ ID NO 4
<211> LENGTH: 760
<212> TYPE: DNA
<213> ORGANISM: Lactobacillus plantarum
<220> FEATURE:
<221> NAME/KEY: misc_feature
<222> LOCATION: (109)..(109)
<223> OTHER INFORMATION: y is c or t
<220> FEATURE:
<221> NAME/KEY: misc_feature
<222> LOCATION: (146)..(146)
<223> OTHER INFORMATION: n is a, t, g, or c
<220> FEATURE:
<221> NAME/KEY: misc_feature
<222> LOCATION: (561)..(561)
<223> OTHER INFORMATION: n is a, t, g, or c
<220> FEATURE:
<221> NAME/KEY: misc_feature
<222> LOCATION: (734)..(734)
<223> OTHER INFORMATION: n is a, t, g, or c

<400> SEQUENCE: 4
```

| | |
|---|---|
| agcgtcagtt acagaccaga cagccgcctt cgccactggt gttcttccat atatctacgc | 60 |
| atttcaccgc tacacatgga gttccactgt cctcttctgc actcaagtyt cccagtttcc | 120 |
| gatgcacttc ttcggttgag ccgaangctt tcacatcaga cttaaaaaac cgcctgcgct | 180 |
| cgctttacgc ccaataaatc cggacaacgc ttgccaccta cgtattaccg cggctgctgg | 240 |
| cacgtagtta gccgtggctt tctggttaaa taccgtcaat acctgaacag ttactctcag | 300 |
| atatgttctt cttaacaac agagttttac gagccgaaac ccttcttcac tcacgcggcg | 360 |
| ttgctccatc agactttcgt ccattgtgga agattcccta ctgctgcctc ccgtaggagt | 420 |
| tgggccgtg tctcagtccc aatgtggccg attaccctct caggtcggct acgtatcatt | 480 |
| gccatggtga gccgttaccc caccatctag ctaatacgcc gcgggaccat ccaaaagtga | 540 |
| tagccgaagc catctttcaa nctcggacca tgcggtccaa gttgttatgc ggtattagca | 600 |
| tctgttttcca ggtgttatcc cccgcttctg ggcaggtttc ccacgtgtta ctcaccagtt | 660 |
| cgccactcac tcaaatgtaa atcatgatgc aagcaccaat caataccaga gttcgttcga | 720 |
| cttgcatgta ttangcacgc cgccagcgtt cgtcctgagc | 760 |

```
<210> SEQ ID NO 5
<211> LENGTH: 739
<212> TYPE: DNA
<213> ORGANISM: Lactobacillus brevis
<220> FEATURE:
<221> NAME/KEY: misc_feature
<222> LOCATION: (560)..(560)
<223> OTHER INFORMATION: n is a, t, g, or c
<220> FEATURE:
<221> NAME/KEY: misc_feature
<222> LOCATION: (715)..(715)
<223> OTHER INFORMATION: n is a, t, g, or c
```

-continued

<400> SEQUENCE: 5

```
acagccgcct tcgccactgg tgttcttcca tatatctacg cattccaccg ctacacatgg        60
agttccactg tcctcttctg cactcaagtc tcccagtttc cgatgcactt ctccggttaa       120
gccgaaggct ttcacatcag acttaaaaaa ccgcctgcgc tcgctttacg cccaataaat       180
ccggacaacg cttgccacct acgtattacc gcggctgctg gcacgtagtt agccgtggct       240
ttctggttaa ataccgtcaa cccttgaaca gttactctca aggtgttct tctttaacaa        300
cagagtttta cgagccgaaa cccttcttca ctcacgcggc attgctccat cagactttcg       360
tccattgtgg aagattccct actgctgcct cccgtaggag tttgggccgt gtctcagtcc       420
caatgtggcc gattaccctc tcaggtcggc tacgtatcat cgtcttggtg ggcctttacc       480
tcaccaacta actaatacgc cgcgggatca tccagaagtg atagccgaag ccacctttca       540
aacaaaatcc atgcggattn tgttgttata cggtattagc acctgtttcc aagtgttatc       600
ccctgcttct gggcagattt ccacgtgtt actcaccagt tcgccactcg cttcattgtt         660
gaaatcagtg caagcacgtc attcaacgga agctcgttcg acttgcatgt attangcatg       720
ccgccagcgt tcgtcctga                                                    739
```

<210> SEQ ID NO 6
<211> LENGTH: 765
<212> TYPE: DNA
<213> ORGANISM: Lactobacillus curvatus
<220> FEATURE:
<221> NAME/KEY: misc_feature
<222> LOCATION: (737)..(737)
<223> OTHER INFORMATION: n is a, t, g, or c

<400> SEQUENCE: 6

```
gcgtcagtta cagaccagac agccgccttc gccactggtg ttcttccata tatctacgca        60
tttcaccgct acacatggag ttccactgtc ctcttctgca ctcaagtttc ccagtttccg       120
atgcacttct tcggttgagc cgaaggcttt cacatcagac ttaagaaacc gcctgcgctc       180
gctttacgcc caataaatcc ggacaacgct tgccacctac gtattaccgc ggctgctggc       240
acgtagttag ccgtggcttt ctggttggat accgtcacta cctgatcagt tactatcaaa       300
tacgttcttc tccaacaaca gagttttacg atccgaaaac cttcttcact cacgcggcgt       360
tgctccatca gactttcgtc cattgtggaa gattccctac tgctgcctcc cgtaggagtc       420
tgggccgtgt ctcagtccca gtgtggccga ttaccctctc aggtcggcta tgcatcacgg       480
tcttggtgag cctttacctc accaactaac taatgcaccg cgggtccatc ctaaagtgat       540
agccgaaacc atctttcaac cttgcaccat gcggtgctag gttttatgcg gtattagcat       600
ctgtttccaa atgttatccc ccactttagg gcaggttacc cacgtgttac tcacccgtcc       660
gccactcact caaatgttat caatcagaag caagcttctt caatctaacg agagtgcgtt       720
cgacttgcat gtattangca cgccgccagc gttcgtcctg agcca                       765
```

<210> SEQ ID NO 7
<211> LENGTH: 767
<212> TYPE: DNA
<213> ORGANISM: Lactobacillus reuteri
<220> FEATURE:
<221> NAME/KEY: misc_feature
<222> LOCATION: (166)..(166)
<223> OTHER INFORMATION: n is a, t, g, or c
<220> FEATURE:
<221> NAME/KEY: misc_feature
<222> LOCATION: (456)..(456)
<223> OTHER INFORMATION: n is a, t, g, or c

```
<220> FEATURE:
<221> NAME/KEY: misc_feature
<222> LOCATION: (561)..(561)
<223> OTHER INFORMATION: n is a, t, g, or c
<220> FEATURE:
<221> NAME/KEY: misc_feature
<222> LOCATION: (635)..(635)
<223> OTHER INFORMATION: n is a, t, g, or c
<220> FEATURE:
<221> NAME/KEY: misc_feature
<222> LOCATION: (728)..(728)
<223> OTHER INFORMATION: n is a, t, g, or c

<400> SEQUENCE: 7
agcgtcagtt gcagaccaga cagccgcctt cgccactggt gttcttccat atatctacgc    60
attccaccgc tacacatgga gttccactgt cctcttctgc actcaagtcg cccggtttcc   120
gatgcacttc ttcggttaag ccgaaggctt tcacatcaga cctaancaac cgcctgcgct   180
cgctttacgc ccaataaatc cggataacgc ttgccaccta cgtattaccg cggctgctgg   240
cacgtagtta gccgtgactt tctggttgga taccgtcact gcgtgaacag ttactctcac   300
gcacgttctt ctccaacaac agagctttac gagccgaaac ccttcttcac tcacgcggtg   360
ttgctccatc aggcttgcgc ccattgtgga agattcccta ctgctgcctc ccgtaggagt   420
atggaccgtg tctcagttcc attgtggccg atcagnctct caactcggct atgcatcatc   480
gccttggtaa gccgttacct taccaactag ctaatgcacc gcaggtccat cccagagtga   540
tagccaaagc catctttcaa ncaaaagcca tgtggctttt gttgttatgc ggtattagca   600
tctgtttcca aatgttatcc cccgctccgg ggcangttac ctacgtgtta ctcacccgtc   660
cgccactcac tggtgatcca tcgtcaatca ggtgcaagca ccatcaatca gttgggccag   720
tgcgtacnac ttgcatgtat taggcacacc gccggcgttc atcctga              767

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
agagtttgat cctggctcag                                                 20

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
gactaccagg gtatctaatc                                                 20

<210> SEQ ID NO 10
<211> LENGTH: 15
<212> TYPE: DNA
<213> ORGANISM: Artificial Sequence
<220> FEATURE:
<223> OTHER INFORMATION: Synthetic primer

<400> SEQUENCE: 10
gagggtggcg gttct                                                      15
```

```
<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
ctcaccagca cctttgtcca                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
ctccttgtcc gtcaccaacc                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer

<400> SEQUENCE: 13
gcactgagaa aggaggtggg                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
cctgagacca gcagcagaaa                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer

<400> SEQUENCE: 15
aacccctccc ttctcaaact                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
tagaacccac aactgctggc                                              20

<210> SEQ ID NO 17
<211> LENGTH: 18
<212> TYPE: DNA
<213> ORGANISM: Artificial Sequence
<220> FEATURE:
<223> OTHER INFORMATION: Synthetic Primer
```

```
<400> SEQUENCE: 17
ggggaaagga tgccccaa                                                  18

<210> SEQ ID NO 18
<211> LENGTH: 20
<212> TYPE: DNA
<213> ORGANISM: Artificial Sequence
<220> FEATURE:
<223> OTHER INFORMATION: Synthetic Primer

<400> SEQUENCE: 18
acggagctgt ggttaatggg                                                20

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer

<400> SEQUENCE: 19
cctgactggt ggatgtgacc                                                20

<210> SEQ ID NO 20
<211> LENGTH: 21
<212> TYPE: DNA
<213> ORGANISM: Artificial Sequence
<220> FEATURE:
<223> OTHER INFORMATION: Synthetic Primer

<400> SEQUENCE: 20
gcagtcctgg taaatgtggg a                                              21

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer

<400> SEQUENCE: 21
catctccttc tgctgctggt                                                20

<210> SEQ ID NO 22
<211> LENGTH: 20
<212> TYPE: DNA
<213> ORGANISM: Artificial Sequence
<220> FEATURE:
<223> OTHER INFORMATION: Synthetic Primer

<400> SEQUENCE: 22
acaagaatgg cacagagggg                                                20

<210> SEQ ID NO 23
<211> LENGTH: 20
<212> TYPE: DNA
<213> ORGANISM: Artificial Sequence
<220> FEATURE:
<223> OTHER INFORMATION: Synthetic Primer

<400> SEQUENCE: 23
tcattcgttt cctcccaccg                                                20
```

```
<210> SEQ ID NO 24
<211> LENGTH: 20
<212> TYPE: DNA
<213> ORGANISM: Artificial Sequence
<220> FEATURE:
<223> OTHER INFORMATION: Synthetic Primer

<400> SEQUENCE: 24
atctctctgg gctctggctt                                                   20

<210> SEQ ID NO 25
<211> LENGTH: 21
<212> TYPE: DNA
<213> ORGANISM: Artificial Sequence
<220> FEATURE:
<223> OTHER INFORMATION: Synthetic Primer

<400> SEQUENCE: 25
gccagtagct catgttgtag g                                                 21

<210> SEQ ID NO 26
<211> LENGTH: 16
<212> TYPE: DNA
<213> ORGANISM: Artificial Sequence
<220> FEATURE:
<223> OTHER INFORMATION: Synthetic Primer

<400> SEQUENCE: 26
tggccctcgg gttctg                                                       16

<210> SEQ ID NO 27
<211> LENGTH: 20
<212> TYPE: DNA
<213> ORGANISM: Artificial Sequence
<220> FEATURE:
<223> OTHER INFORMATION: Synthetic Primer

<400> SEQUENCE: 27
ggattaagtt ggggcaggga                                                   20

<210> SEQ ID NO 28
<211> LENGTH: 20
<212> TYPE: DNA
<213> ORGANISM: Artificial Sequence
<220> FEATURE:
<223> OTHER INFORMATION: Synthetic Primer

<400> SEQUENCE: 28
aaagcagttg ggagtctggc                                                   20
```

PROBIOTIC BACTERIA ISOLATED FROM WOLVES AND RELATED COMPOSITIONS AND METHODS

RELATED APPLICATIONS

This application claims priority to U.S. Provisional Patent Application No. 62/720,180, filed Aug. 21, 2018, the entire contents of which are incorporated herein by reference.

FIELD OF THE DISCLOSURE

The present disclosure relates to probiotics. More particularly, the present disclosure relates to isolated strains of probiotic bacteria from free ranging wolves and related compositions and methods.

BACKGROUND

The gastrointestinal (GI) tracts of most mammals are colonized by native micro-organisms forming a microbiota. In a healthy animal, there is a balance between beneficial or benign bacteria and pathogenic bacteria. Intestinal dysbiosis refers to an imbalance of the microbiota of the intestine. Dysbiosis in microbiota of the intestine may cause a shift in the balance of immunostimulatory cytokines in the GI tract. This shift in immunostimulatory cytokines may in turn alter the balance of the inflammatory signals in the gut, causing diarrhea and other acute and chronic GI disorders.

Probiotics may help to restore the balance of beneficial bacteria in the GI tract and therefore may be useful in treating intestinal dysbiosis and GI disorders.

Although probiotics have conventionally been used only in humans, there is increasing interest in use of probiotics in companion animals such as dogs. However, commercially-available canine probiotics are generally of human origin and are not optimal for animals since probiotic bacteria typically possess host-specific traits (Oh et al., "Diversification of the gut symbiont Lactobacteria reuteri as a result of host-driven evolution", *ISME J*, 2010, Vol 4: pp 377-387; Frese et al., "The evolution of host specialization in the vertebrate gut symbiont *Lactobacillus reuteri*", *PloS Genet.*, 2011. 7:e1001314).

Some canine probiotics isolated from dogs are known. However, the nutritional profile of commercial pet foods may result in alterations in the intestinal microbiome of domestic dogs and not all probiotics isolated from domestic dogs may be effective in counteracting intestinal dysbiosis.

SUMMARY

In one aspect, there is provided an isolated strain from a wolf for use as a probiotic in a subject.

In some embodiments, the subject is a canine subject.

In some embodiments, the canine subject is a domestic dog.

In some embodiments, the isolated strain is selected from a *Lactobacillus* species or an *Enterococcus* species.

In some embodiments, the isolated strain is selected from *Lactobacillus reuteri*, *Lactobacillus animalis*, *Enterococcus faecium*, *Lactobacillus plantarum*, *Lactobacillus brevis*, or *Lactobacillus curvatus*.

In some embodiments, the isolated strain is selected from *Lactobacillus reuteri* strain WF-1 IDAC Accession number 181218-01; *Lactobacillus animalis* strain WF-2 IDAC Accession number 181218-02; *Enterococcus faecium* strain WF-3 IDAC Accession number 181218-03; *Lactobacillus plantarum* strain WF-4 IDAC Accession number 181218-04; *Lactobacillus brevis* strain WF-5 IDAC Accession number 181218-05; *Lactobacillus curvatus* strain WF-6 IDAC Accession number 181218-06; *Lactobacillus reuteri* strain WF-7 IDAC Accession number 181218-07; or mutant strains thereof.

In another aspect, there is provided a composition comprising at least one isolated strain of wolf probiotic bacteria.

In some embodiments, the composition further comprises one or more of a prebiotic, an additional pharmaceutical or nutritional ingredient, or a pharmaceutically or nutritionally acceptable excipient.

In some embodiments, the composition is in the form of a dietary supplement.

In some embodiments, the composition is in the form of a food product.

In some embodiments, the food product comprises a dog food or a dog treat.

In some embodiments, the at least one isolated strain of wolf probiotic bacteria is selected from a *Lactobacillus* species or an *Enterococcus* species.

In another aspect, there is provided a method for preparing a composition comprising: providing at least one isolated strain of wolf probiotic bacteria; providing at least one ingredient; and combining the at least one isolated strain of wolf probiotic bacteria and the at least one ingredient.

In some embodiments, the at least one ingredient is an edible ingredient.

In some embodiments, the at least one isolated strain of wolf probiotic bacteria is provided in the form of a powder or a liquid.

In some embodiments, the at least one isolated strain of wolf probiotic bacteria is selected from a *Lactobacillus* species or an *Enterococcus* species.

In another aspect, there is provided a method for treating or preventing intestinal dysbiosis in a subject comprising administering at least one isolated strain of wolf probiotic bacteria to a subject.

In some embodiments, the subject is a domestic dog.

In some embodiments, the at least one isolated strain of wolf probiotic bacteria is administered orally, enterally, or rectally.

In some embodiments, the at least one isolated strain of wolf probiotic bacteria is selected from a *Lactobacillus* species or an *Enterococcus* species.

In another aspect, there is provided a use of at least one isolated strain of wolf probiotic bacteria in the preparation of a medicament for treating or preventing intestinal dysbiosis in a subject.

In some embodiments, the subject is a domestic dog.

In some embodiments, the at least one isolated strain of wolf probiotic bacteria is selected from a *Lactobacillus* species or an *Enterococcus* species.

In another aspect, there is provided *Lactobacillus reuteri* strain WF-1 IDAC Accession number 181218-01.

In another aspect, there is provided *Lactobacillus animalis* strain WF-2 IDAC Accession number 181218-02.

In another aspect, there is provided *Enterococcus faecium* strain WF-3 IDAC Accession number 181218-03.

In another aspect, there is provided *Lactobacillus plantarum* strain WF-4 IDAC Accession number 181218-04.

In another aspect, there is provided *Lactobacillus brevis* strain WF-5 IDAC Accession number 181218-05.

In another aspect, there is provided *Lactobacillus curvatus* strain WF-6 IDAC Accession number 181218-06.

In another aspect, there is provided *Lactobacillus reuteri* strain WF-7 IDAC Accession number 181218-07.

Other aspects and features of the present disclosure will become apparent, to those ordinarily skilled in the art, upon review of the following description of the specific embodiments of the disclosure.

BRIEF DESCRIPTION OF THE DRAWINGS

Some aspects of the disclosure will be described in greater detail with reference to the accompanying drawings. In the drawings:

FIG. 2A shows a 16S rDNA sequence of *Lb. reuteri* WF-1 (SEQ. ID NO: 1); FIG. 2B shows a 16S rDNA sequence of *Lb. animalis* WF-2 (SEQ. ID NO: 2); FIG. 2C shows a 16S rDNA sequence of *Ec. faecium* WF-3 (SEQ. ID NO: 3); FIG. 2D shows a 16S rDNA sequence of *Lb. plantarum* WF-4 (SEQ. ID NO: 4); FIG. 2E shows a 16S rDNA sequence of *Lb. brevis* WF-5 (SEQ. ID NO: 5); FIG. 2F shows a 16S rDNA sequence of *Lb. curvatus* WF-6 (SEQ. ID NO: 6); FIG. 2G shows a 16S rDNA sequence of *Lb. reuteri* WF-7 (SEQ. ID NO: 7);

DETAILED DESCRIPTION OF EMBODIMENTS

Figure 1:
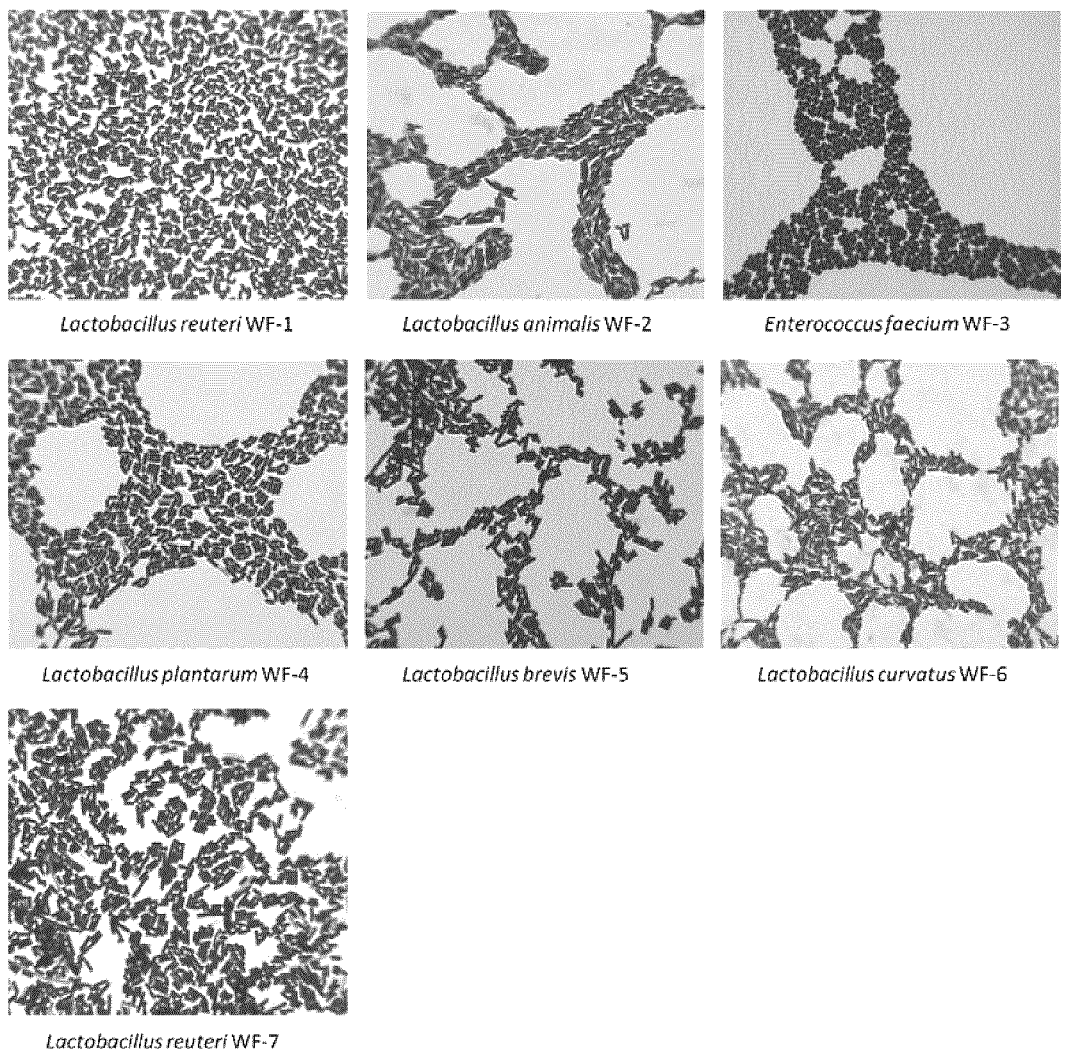
FIG. 1 shows bacterial morphologies of isolated strains *Lactobacillus reuteri* WF-1, *Lactobacillus animalis* WF-2, *Enterococcus faecium* WF-3, *Lactobacillus plantarum* WF-4, *Lactobacillus brevis* WF-5, *Lactobacillus curvatus* WF-6, and *Lactobacillus reuteri* WF-7, according to some embodiments.

Generally, the present disclosure provides isolated strains of gastrointestinal bacteria from wolves for use as probiotics. In some embodiments, the isolated strains are for use as probiotics in canine subjects such as domestic dogs. In some embodiments, the isolated strains may be used to treat or prevent intestinal dysbiosis in the subject. Also provided is a composition comprising at least one isolated strain of wolf probiotic bacteria and a related method for making same.

As used herein, "probiotic" refers to a microbial cell culture or preparation that has at least one beneficial effect on a host organism. The beneficial effects on the host organism may include, for example, a beneficial effect on the host's digestive system and/or immune and/or brain-gut-microbiome systems. Embodiments are not limited by the specific beneficial effects described herein.

The present disclosure provides isolated strains of gastrointestinal bacteria from free ranging wolves for use as a probiotic. As used herein, "wolf" refers to an animal of the *Canis lupus* species, including any known subspecies, with the exception of *Canis lupus familiaris*. A wolf may also be known as a gray wolf, grey wolf, timber wolf, or tundra wolf. In some embodiments, the wolves are free-ranging wolves native to Prince Albert National Park in Saskatchewan, Canada.

As used herein, "gastrointestinal bacteria" refer to bacteria that are native to the gastrointestinal tract of an animal. As used herein, "isolated" or "isolate", when used in reference to a strain of bacteria, refers to bacteria that have been separated from their natural environment. In some embodiments, the isolated strain or isolate is a biologically pure culture of a specific strain of bacteria. As used herein, "biologically pure" refers to a culture that is substantially free of other strain of organisms.

In some embodiments, the isolated strain of gastrointestinal bacteria from a wolf is isolated from wolf feces. In some embodiments, the isolated stain may be isolated from wolf feces using the methods described in the Examples below.

The isolated strain of gastrointestinal bacteria from a wolf may be used as a probiotic in a subject. In some embodiments, the subject is a canine subject. As used herein, "canine" refers to an animal of the *Canis* genus including wolves, dogs (as defined below), and hybrids thereof.

In some embodiments, the canine subject is a domestic dog. As used herein, "dog" or "domestic dog" refers to an animal of the *Canis lupus familiaris* subspecies. Some taxonomic authorities alternatively recognize domestic dogs as a distinct species *Canis familiaris*. In some embodiments, the dog is an adult dog. In other embodiments, the dog is at any other stage of development.

In some embodiments, the isolated strain is a strain of lactic acid bacteria. In some embodiments, the isolated strain is a *Lactobacillus* species (also known as lactobacilii). In other embodiments, the isolated strain is an *Enterococcus* species. In other embodiments, the isolated strain is any other genus of gastrointestinal bacteria native to a wolf gastrointestinal tract.

In some embodiments, the isolated strain of gastrointestinal bacteria is one of *Lactobacillus reuteri*, *Lactobacillus animalis*, *Enterococcus faecium*, *Lactobacillus plantarum*, *Lactobacillus brevis*, and *Lactobacillus curvatus*.

In some embodiments, the isolated strain of gastrointestinal bacteria is one of the strains listed in Table 1 below. For each bacterial strain in Table 1, a biologically pure stock of each isolate was deposited in the International Depositary Authority of Canada (IDAC) (1015 Arlington Street, Winnipeg, Manitoba, Canada R3E 3R2) under the Budapest Treaty on Dec. 18, 2018. Gram staining results showing the bacterial morphologies of each of the isolated strains of Table 1 are shown in FIG. 1.

TABLE 1

| Wolf Feces | Date of Feces Collected on | Location of Feces Collected | Species of Wolf | Lactic Acid Bacteria Isolated | IDAC Accession Number |
|---|---|---|---|---|---|
| #1 | Mar. 23, 2017 | Prince Albert National Park, Saskatchewan, Canada | Canis lupus | Lactobacillus reuteri WF-1 | 181218-01 |
|  |  |  |  | Lactobacillus animalis WF-2 | 181218-02 |
| #2 | Sep. 6, 2017 | Prince Albert National Park, Saskatchewan, Canada | Canis lupus | Enterococcus faecium WF-3 | 181218-03 |
|  |  |  |  | Lactobacillus plantarum WF-4 | 181218-04 |
|  |  |  |  | Lactobacillus brevis WF-5 | 181218-05 |
|  |  |  |  | Lactobacillus curvatus WF-6 | 181218-06 |
|  |  |  |  | Lactobacillus reuteri WF-7 | 181218-07 |

In some embodiments, a 16S ribosomal DNA (rDNA) sequence can be used to identify genus and species of bacteria. Sequencing of 16S rDNA sequences may be performed using the methods described in the Examples below. The 16S rDNA sequences of the isolated strains of Table 1 are listed in Table 2 and shown in FIGS. 2A-2G:

TABLE 2

| Strain | 16S rDNA Sequence | Figure Showing 16S rDNA Sequence |
|---|---|---|
| Lactobacillus reuteri WF-1 | SEQ. ID NO: 1 | FIG. 2A |
| Lactobacillus animalis WF-2 | SEQ. ID NO: 2 | FIG. 2B |
| Enterococcus faecium WF-3 | SEQ. ID NO: 3 | FIG. 2C |
| Lactobacillus plantarum WF-4 | SEQ. ID NO: 4 | FIG. 2D |
| Lactobacillus brevis WF-5 | SEQ. ID NO: 5 | FIG. 2E |
| Lactobacillus curvatus WF-6 | SEQ. ID NO: 6 | FIG. 2F |
| Lactobacillus reuteri WF-7 | SEQ. ID NO: 7 | FIG. 2G |

In some embodiments, the isolated strain is a mutant of one of the strains listed in Table 1. As used herein, a "mutant" or a "mutant strain" refers to a bacterial strain that has at least 95% homology, at least 96% homology, at least 97% homology, at least 98% homology, at least 99% homology, or at least 99.5% homology to the 16S rDNA sequence of a reference bacterial strain but that otherwise has one or more DNA mutations in one or more other DNA sequences in the bacterial genome. DNA mutations may include base substitutions including transitions and transversions, deletions, insertions, and any other type of natural or induced DNA modification.

In some embodiments, the isolated strain may be further characterized by whole genome sequencing, as described in more detail in the Examples below. In some embodiments, the isolated strain has at least one adhesion gene, bacteriocin gene, copper homeostasis gene, and/or bile hydrolysis gene. In some embodiments, the isolated strain does not have any genes encoding toxins or superantigens.

The isolated strain may be capable of probiotic activity in the subject. As used herein, "probiotic activity" refers to the ability of the bacteria of the isolated strain to produce at least one beneficial effect in the subject. In some embodiments, the isolated strain of bacteria is capable of surviving and colonizing in the gastrointestinal tract of the subject to provide the beneficial effect to the subject.

In some embodiments, the bacteria of the isolated strain are tolerant to low pH, indicating that the bacteria may be capable of surviving passage through the acidic canine stomach. As used herein, "low pH" refers to a pH of 6.9 or less. In some embodiments, the bacteria are able to survive in vitro at a pH of about 2.5 to about 6.9 for at least 2 hours. In some embodiments, the bacteria are able to survive in vitro at a pH of about 3.0 to about 6.9 for at least 6 hours. Survival may be measured using plate count methods, as described in the Examples below, or any other suitable method. As used herein, "survive" means that the viable cell count of a test culture (as measured in colony forming units (CFU) per mL) is above detection limit [$1.7 \log_{10}(\text{CFU/mL})$ or 50 CFU/mL].

In some embodiments, the bacteria of the isolated strain are tolerant to the presence of bile salt, indicating that the bacteria may survive the passage through the canine intestine. In some embodiments, the bacteria are able to survive in vitro in the presence of 5% bile salts for at least 24 hours.

In some embodiments, the bacteria of the isolated strain are tolerant to the presence of at least one gastric digestive enzyme. In some embodiments, the bacteria are able to survive in vitro for at least 2 hours in SGF at pH 3.0 in the presence of pepsin (3.2 mg/mL). In some embodiments, the bacteria of the isolated strain are tolerant to the presence of at least one intestinal digestive enzyme. In some embodiments, the bacteria are able to survive in vitro in simulated intestinal fluid (SIF) for at least 24 hours at pH 6.8 in the presence of pancreatin (10 mg/mL).

In some embodiments, the bacteria of the isolated strain have autoaggregation ability, indicating that the bacterial cells may be able to bind host intestinal epithelial cells in the subject to facilitate colonization of the gastrointestinal tract. As used herein, "autoaggregation" or "autoaggregate" refers to the bacterial cells binding to one another to floc out of solution. Autoaggregation may be measured by measuring the $OD_{600}$ of a stationary liquid bacterial culture over time, as described in more detail in the Examples below, or by any other suitable method.

In some embodiments, the bacteria of the isolated strain have high cell surface hydrophobicity, indicating that the bacterial cells may be able to adhere to host cells in the subject to facilitate colonization of the gastrointestinal tract. Cell surface hydrophobicity may be measured by Microbial Adhesion to Hydrocarbons (MATH), as described in more detail in the Examples below, or by any other suitable method.

In some embodiments, the bacteria of the isolated strain are able to bind to canine cells in vitro. In some embodiments, the bacteria are able to bind canine epithelial cells in vitro, for example, Madin-Darby Canine Kidney (MDCK (NBL-2), Canis familiaris ATCC CCL-34)) cells. In some embodiments, the bacteria are able to bind canine macrophage-like cells in vitro, for example, DH82 cells (Canis familiaris ATCC CRL-10389). In other embodiments, the bacteria may be able to bind any other suitable type of canine cell.

In some embodiments, the bacteria of the isolated strain are able to modulate expression of at least one anti-inflammatory or pro-inflammatory cytokine by host immune cells.

Non-limiting examples of anti-inflammatory or pro-inflammatory cytokines include IL-10, IL-6, TGF-β and any other known anti-inflammatory or pro-inflammatory cytokine. In some embodiments, the ability to stimulate expression of at least one anti-inflammatory cytokine can be measured by incubating cytokine-expressing cells in the presence of bacteria of the isolated strain and measuring cytokine expression by real-time quantitative PCR (RT-qPCR), as described in more detail in the Examples below, or by any other suitable method.

In some embodiments, the bacteria of the isolated strain are able to inhibit growth of at least one pathogenic or spoilage microorganism. In some embodiments, the bacteria produce an inhibitory substance that inhibits the growth of at least one pathogenic or spoilage microorganism. In some embodiments, the pathogenic microorganism is a canine intestinal pathogen. Examples of microorganisms that may be inhibited by the isolated strain include Enteropathogenic *Escherichia coli* E2348/69, *Salmonella enterica* serovar *Typhimurium*, *Listeria monocytogenes*, *Staphylococcus aureus*, *Enterococcus faecalis*, *Clostridium perfringens*, and *Clostridium difficile*. However, embodiments are not limited to the microorganisms described herein. The production of inhibitory substances may be tested by growing an indicator strain (e.g. a strain of a pathogenic or spoilage microorganism) in the presence of the isolated strain, as described in more detail in the Examples below. If the isolated strain produces inhibitory substances, growth of the indicator strain may be inhibited presence of the isolates strain. Alternatively, the inhibitory activity of the isolated strain may be tested by any other suitable method.

In some embodiments, the bacteria of the isolated strain are susceptible to at least one antibiotic. Antibiotic susceptibility may be desirable to prevent the transfer of antibiotic resistance genes to other bacteria, including pathogenic bacteria. Antibiotic susceptibility may be tested using the methods described in the Examples below, or by any other suitable method. The lowest antibiotic concentration for which no bacteria growth is observed is the minimum inhibitory concentration (MIC). In some embodiments, the isolated strain has an MIC value for at least one antibiotic that is at or below the MIC breakpoint value set by the European Food Safety Authority (EFSA). Examples of antibiotics to which the isolated strain may be susceptible include, for example, ampicillin, gentamycin, kanamycin, streptomycin, erythromycin, clindamycin, tetracycline and chloramphenicol. However, embodiments are not limited to the antibiotics described herein.

In some embodiments, a lyophilized (freeze-dried) form of the isolated strain is substantially stable for a suitable shelf-life period. As used herein, "substantially stable" means that at least 50% of the bacterial cells are still viable at the end of a given time period, as measured in CFU/g. In some embodiments, the lyophilized form of the isolated strain is substantially stable for at least 10 weeks at 4° C.

The isolated strains of wolf probiotic bacteria described above may be used to improve and/or maintain the health of the subject. In some embodiments, at least one isolated strain of wolf probiotic bacteria may be used to treat or prevent intestinal dysbiosis in the subject or treat the subject for a health condition or disorder. As used herein, "treat" or "treatment" refers to obtaining a desired pharmacologic and/or physiologic effect. The effect can be prophylactic in terms of completely or partially preventing a health condition or symptom thereof and/or can be therapeutic in terms of a partial or complete cure for the health condition and/or adverse effect attributable to the health condition. In some embodiments, at least one isolated strain of wolf probiotic bacteria may be used to treat or prevent diarrhea in the subject. In other embodiments, at least one strain of wolf probiotic bacteria may be used to provide any other health benefit to the subject. In some embodiments, at least one isolated strain of wolf probiotic bacteria may be used in the preparation of a medicament for treatment or prevention of intestinal dysbiosis, diarrhea, or any other suitable health condition.

Without being limited by theory, it is believed that some commercial pet foods have a materially different nutritional profile compared to the fats, proteins and carbohydrates within the prey hunted and consumed by wolves. Such nutritional profile differences may result in alterations to the intestinal microbiome in domestic dogs. By introducing gastrointestinal bacteria from a wolf into the GI tract of a dog, the dog's intestinal microbiome may shift towards more of an ancestral state and thereby treat or prevent dysbiosis.

The isolated strain may be administered to the subject in an effective amount. As used herein, "effective amount" refers to an amount of the isolated strain that provides at least one health benefit to the subject. The effective amount may vary based on a number of factors including but not limited to the specific isolated strain being administered and its characteristics; the age, weight, sex, diet, and general health of the subject; the mode and time of administration; the severity of the condition being treated; the nature of any concurrent therapies or medications; and any other relevant factor.

In some preferred embodiments, the isolated strain is orally administrable to the subject. In other embodiments, the isolated strain may be enterally and/or rectally administrable to the subject. In some embodiments, the isolated strain may be administered to the subject at any suitable interval including, for example, at least once per month, at least once per week, or at least once per day. In some embodiments, per 20 lbs of body weight of the subject, about 1 billion CFU per daily serving may be orally administered to the subject.

In some embodiments, the isolated strain is administrable in a viable form. In some embodiments, the isolated strain is administrable in a lyophilized (freeze-dried) form. In other embodiments, the isolated strain is administrable as a liquid suspension.

Also provided is a composition comprising at least one isolated strain of wolf probiotic bacteria. As used herein "wolf probiotic bacteria" refers to bacteria with probiotic activity isolated from a wolf. Any of the isolated strains described above may be used as the wolf probiotic bacteria in the compositions described herein.

In some embodiments, the composition may comprise two or more isolated strains of wolf probiotic bacteria. In some embodiments, the composition may further comprise at least one additional strain of probiotic bacteria isolated from an animal other than a wolf. In some embodiments, the additional strain of probiotic bacteria may be isolated from a domestic dog species.

In some embodiments, the composition may further comprise at least one prebiotic. As used herein, "prebiotic" refers to a substance that stimulates the growth or activity of at least one beneficial micro-organism. In some embodiments, the prebiotic compound induces the growth or activity of at least one isolated strain of wolf probiotic bacteria. Non-limiting examples of suitable prebiotics include inulin, pectin, beta-glucans, fructooligosaccharides (FOS), galactooligosaccharides (GOSs), xylooligosaccharides (XOS), resistant starch, organic molecules such as humic and fulvic acid, and any other suitable prebiotic.

In some embodiments, the composition may further comprise at least one additional pharmaceutical or nutritional ingredient. In some embodiments, the additional ingredient comprises at least one cannabinoid, for example, cannabidiol (CBD). In some embodiments, the additional ingredient comprises chondroitin sulfate. In other embodiments, the additional ingredient comprises at least one vitamin, mineral, fiber, fatty acid, amino acid, or any other suitable pharmaceutical or nutritional ingredient.

In some embodiments, the composition may further comprise at least one encapsulation material. Non-limiting examples of suitable encapsulation materials include polysaccharides such as alginate, plant/microbial gums, chitosan, starch, k-carrageenan, cellulose acetate phthalate; proteins such as gelatin or milk proteins; fats; and any other suitable encapsulation material. The isolated strain may be encapsulated in the encapsulated material by spray drying, extrusion, gelation, droplet extrusion, emulsion, freeze-drying, or any other suitable encapsulation method. Encapsulation of the bacterial cells of the isolated strain may protect the cells and extend the shelf-life of the composition.

In some embodiments, the composition is an ingestible composition. As used herein, "ingestible" refers to a substance that is orally consumable by the subject.

In some embodiments, the ingestible composition is in the form of a dietary supplement. The dietary supplement may be in the form of a powder, a capsule, a gel capsule, a microcapsule, a bead, a tablet, a chewable tablet, a gummy, a liquid, or any other suitable form of dietary supplement.

In some embodiments, the dietary supplement may further comprise at least one pharmaceutically or nutritionally acceptable excipient. Non-limiting examples of suitable excipients include fillers, binders, carriers, diluents, stabilizers, lubricants, glidants, coloring agents, flavoring agents, coatings, disintegrants, preservatives, sorbents, sweeteners and any other pharmaceutically or nutritionally acceptable excipient. In embodiments in which the dietary supplement is in the form of a capsule, the dietary supplement may further comprise a suitable encapsulation material, including but not limited to, polyvinyl alcohol (PVA), polyvinylpyrrolidone (PVP), alginates, gelatin, and any other suitable encapsulation material.

In some embodiments, the ingestible composition is in the form of a food product. In some embodiments, the food product is any form suitable for a canine subject, particularly a domestic dog. In some embodiments, the food product is a solid food product. In some embodiments, the solid food product may be dry, wet, semi-moist, frozen, dehydrated, freeze-dried, or in any other suitable form. Examples of suitable solid food products include but are not limited to dog foods such as kibble, biscuits, chews, wet dog food, raw dog food including raw meat, freeze-dried yogurt, and others. In some embodiments, the solid food product may in the form of a dog treat including, for example, a freeze-dried dog treat.

In some embodiments, the solid food product is formulated with at least one isolated strain of wolf probiotic bacteria therein. In other embodiments, at least one isolated strain may be added to the solid food product post-production.

In some embodiments, the ingestible composition may be in the form of a surface coating for a solid food product. In some embodiments, the surface coating comprises a carrier to allow the bacteria to adhere to the surface of the solid food product. The carrier may be, for example, an edible oil or any other suitable carrier. As one example, an oil-based surface coating can be applied to kibbled dog food post-production and post-cooling.

In other embodiments, the ingestible composition may be provided in a powder form suitable to sprinkle onto the surface of the solid food product. In other embodiments, the ingestible composition may be provided in a liquid form to spray, pour, or drop onto the surface of the solid food product.

In other embodiments, the food product is a liquid food product. Examples of liquid food products include but are not limited to beverages, broths, oil suspensions, gravies, milk-based products, liquid or semi-solid yogurt, and others.

In some embodiments, the liquid food product is formulated with at least one isolated strain of wolf probiotic bacteria therein. In other embodiments, at least one isolated strain may be added to the liquid food product post-production. In some embodiments, the ingestible composition may be provided in a powder form and the powder may be dissolved in water, milk, or any other suitable liquid to form the liquid food product. In other embodiments, the ingestible composition may be provided in a liquid form and may be mixed with water, milk, or any other suitable liquid to form the liquid food product. In other embodiments, the liquid food product may be sprayed, poured, or dropped directly into the subject's mouth.

In other embodiments, the ingestible composition may be in any other form suitable for ingestion by a canine subject, particularly a domestic dog. In other embodiments, the composition may be in a non-ingestible form, for example, as a suppository, or any other suitable form.

Also provided herein is a method of making an ingestible composition. The method may be used to make embodiments of the ingestible compositions described herein.

Figure 3:
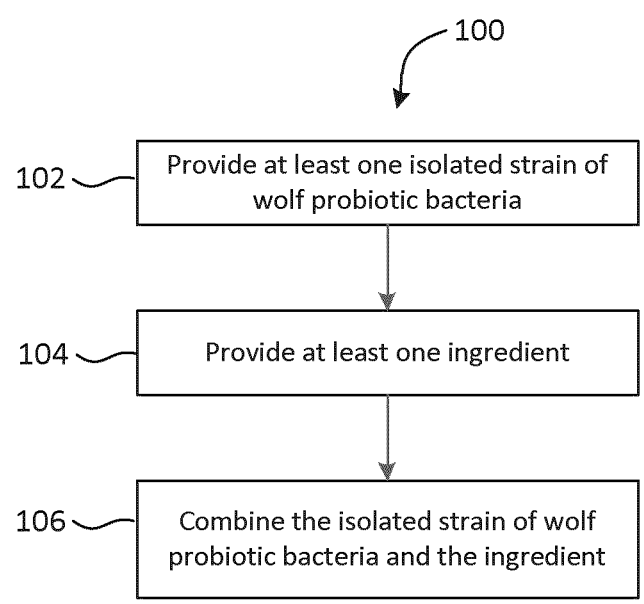
FIG. 3 is a flow chart of a method for making an ingestible composition, according to some embodiments.

FIG. 3 is a flowchart of an exemplary method 100 for making a composition, according to some embodiments. At block 102, at least one isolated strain of wolf probiotic bacteria is provided. At block 104, at least one ingredient is provided. The term "providing" in this context may refer to making (including isolating or culturing), receiving, buying, or otherwise obtaining the isolated strain and the ingredient. At block 106, the isolated strain of wolf probiotic bacteria is combined with the ingredient.

In some embodiments, the isolated strain is at least one of the isolated strains listed in Table 1. In some embodiments, the isolated strain is in a powder form. In other embodiments, the isolated strain is in a liquid form.

In some embodiments, the ingredient is an edible ingredient. In some embodiments, the edible ingredient is at least one pharmaceutically or nutritionally acceptable excipient as described above for dietary supplements. In other embodiments, the edible ingredient is one of the solid or liquid food products described above or any components thereof.

In some embodiments, the isolated strain and the edible ingredient are combined during production of the dietary supplement, solid food product, or liquid food product. In some embodiments, the isolated strain is combined with the solid or liquid food product after the solid or liquid food product is produced.

In some embodiments, the isolated strain is in a powder form and the isolated strain is combined with the at least one edible ingredient by sprinkling the powder on a solid food product. In other embodiments, the isolated strain is in a liquid form and the isolated strain is sprayed, poured, or dropped onto the solid food product. In other embodiments, the isolated strain is mixed with an edible oil and used to coat a solid food product.

In some embodiments, the isolated strain is in a powder form and the isolated strain is combined with the at least one edible ingredient by mixing the powder with water, milk, or any other edible liquid. In other embodiments, the isolated strain is in liquid form and is mixed with the edible liquid.

In other embodiments, the isolated strain may be combined with the ingredient using any suitable means.

Without any limitation to the foregoing, the present strains, compositions, uses, and methods are further described by way of the following examples.

Example 1—Bacterial Isolation

Feces samples from free ranging wolves were collected from Prince Albert National Park in Saskatchewan, Canada, which is distant from cities, human populations, and farming areas. The wolves can range freely and are distant from chemicals utilized by humans, such as pesticides and antibiotics. All feces samples were shipped to Edmonton, Alberta, Canada in a Styrofoam™ box with icepacks and were kept frozen upon receipt until further analysis.

Lactic acid bacteria (LAB) were isolated from the free ranging wolf feces samples using a three-step isolation method described below.

Step I (Selective Enrichment): A pea-sized piece of feces was collected and inoculated into 30 mL of MRS (De Man, Rogosa, and Sharpe) nutrient broth containing with 20 μg/mL nalidixic acid. The feces/broth mixture was mixed well by vortexing and then incubated at 37° C. for 24 h (hours) under airtight conditions.

Step II (Selective Plating): The feces/broth mixture was centrifuged at 5,000 rpm for 5 minutes to pellet the fecal matter. The resulting liquid upper phase (i.e. supernatant) was transferred to a new sterile 50 mL conical tube. The supernatant was centrifuged at 11,000 rpm for 10 minutes to concentrate/pellet the bacteria. Following centrifugation, the supernatant was removed and discarded and the cell pellet was resuspended in 500 μL of MRS broth. One hundred μL of re-suspended bacterial culture was spread plated onto a LAMVAB (*Lactobacillus* anaerobic MRS with vanomycin and bromocresol green) agar plate (5.2% MRS broth, 0.25 mg/mL Cysteine-HCl, 0.025 mg/mL Bromocresol green, 2 mg/mL Vancomycin-HCl, and 2% agar; Hartemink et al., "LAMVAB—a new selective medium for the isolation of lactobacilli from faeces", *Journal of Microbiological Methods* 1997, Vol. 29, pp: 77-84). All agar plates were subsequently incubated at 37° C. for 48 to 72 hours under ambient conditions.

Step III (Single Colony Purification): Single colonies or bacterial lawn from a LAMVAB agar plate were streaked onto MRS agar plates and incubated at 37° C. for 48 h. Single colonies on an MRS agar plate were re-streaked on a new MRS agar plate. This step was repeated until a pure culture on an agar plate was achieved.

All isolates were grouped based on their origin i.e. host (wolf feces collected on different dates or from different spots were considered to be from different wolves) and colony morphologies. Typical isolates from each host were selected for further analysis.

One single colony of each isolate was inoculated into 10 mL of MRS broth and incubated at 37° C. for 24 h. The fully-grown culture was centrifuged at 11,000 rpm for two minutes. The resulting supernatant was discarded and the cell pellet was re-suspended with 1.5 mL of fresh MRS broth, followed by adding 0.5 mL of 80% glycerol and mixing well by pipetting. The glycerol culture stock was stored at −80° C. for long term storage and further analysis.

Seven isolates of wolf probiotic bacteria, labeled WF-1, WF-2, WF-3, WF-4, WF-5, WF-6, and WF-7, were obtained using the methods described above.

Example 2—Isolate Identification

Isolate Cultivation

One loopful of each frozen culture stock was streaked on an MRS agar plate and incubated at 37° C. for 48 h. One single colony was inoculated into 5 mL of MRS broth and incubated at 37° C. for 24 h. One percent of the inoculum (50 μL) was sub-cultured into 5 mL of MRS broth and incubated at 37° C. for 24 h. The fully-grown culture was ready for further analysis.

Isolate Identification by Gram Staining

A Gram-staining kit (Sigma Aldrich™) containing solutions of crystal violet, Gram's iodine, decolorizing fluid, and safranin was used in this study. One mL of fully-grown culture was centrifuged and the supernatant was removed. The cell pellet was resuspended with sterile water. Ten μL of each bacterial resuspension was spread on a microscope glass slide and allowed to air dry. The smear was gently flooded with crystal violet and let stand for 1 minute. The slide was tilted slightly and rinsed with water. The smear was gently flooded with Gram's iodine and let stand for 1 minute. The slide was tilted slightly and rinsed with water. The smear was decolorized with decolorizing fluid for 10 seconds. The slide was tilted slightly and rinsed with water. The smear was gently flooded with safranin to counterstain and let stand for 45 seconds. The slide was tilted slightly and rinsed with water. The slide was blotted dry before being viewed under a light-microscope with oil-immersion.

The Gram-stained bacteria were visualized using a 100× lens on an OMAX™ LED 40×-2000× Digital Binocular Biological Compound Microscope and photos were obtained using a 3.0 MP USB camera connected to the microscope. Gram-positive, rod-shaped or sphere-shaped bacteria were selected for further analysis. The Gram-staining results showing the bacterial morphologies of the seven isolates are shown in FIG. 1.

Isolate Identification by 16S rDNA Sequencing (Sanger Sequencing)

To identify the isolates at the species level, the gene encoding the 16S ribosomal RNA (rRNA) was amplified by PCR and sequenced by Sanger Sequencing.

Colony polymerase chain reaction (PCR) with bacterium specific primers 8F, SEQ ID NO:8 (nucleotide sequence: AGA GTT TGA TCC TGG CTC AG), and 805R, SEQ ID NO:9 (nucleotide sequence: GAC TAC CAG GGT ATC TAA TC) was used to amplify the conserved regions of the 16S rRNA gene. Each PCR reaction mixture had a total volume of 50 μL and contained 5 μL of 10×PCR buffer, 2 μL of dNTP (10 mM), 0.5 μL of forward primer 8F (10 μM), 0.5 μL of reverse primer 805R (10 μM), 0.5 μL of Taq polymerase (5 U/μL), and 2 μL of cell suspension ($1\times10^9$ CFU/mL) as template.

PCR products were separated by 1% agarose gel electrophoresis (110V, 60 min) and visualized under UV (ultraviolet) light. The target amplicon was about 800 bp. Once the correct sized band was confirmed, the remaining PCR product was purified using a GeneJET™ PCR product purification kit (Thermo Scientific™). The concentrations of PCR products were determined using a Nanodrop™ spectrophotometer. Each sample was submitted for Sanger Sequencing using either primer 8F or 805R. Sequencing was performed at The Applied Genomics Centre™ (TAGC) at the University of Alberta. Resulting sequences and chromatograms were viewed using ContigExpress™ software and genus and species were determined using the Basic Local Alignment Search Tool (BLAST) nucleotide search algorithm.

The 16S rDNA sequencing results for the seven isolates are shown in FIGS. 2A to 2G. All isolates were identified as: *Lactobacillus reuteri, Lactobacillus animalis, Enterococcus faecium, Lactobacillus plantarum, Lactobacillus brevis, Lactobacillus curvatus,* and *Lactobacillus reuteri.*

Isolate Identification by RAPD Profiling

To eliminate duplicate strains from all isolates, random amplified polymorphic DNA (RAPD) PCR was used. This experiment was performed to compare isolates from the same host (referring to wolf feces collected on the same day and at the same place/area), not isolates from different sources. Colony PCR was performed using the M13 primer, SEQ ID NO:10 (nucleotide sequence GAGGGTGGCGGTTCT; Rossetti and Giraffa, "Rapid identification of dairy lactic acid bacteria by M13-generated, RAPD-PCR fingerprint databases", *J Microbiol Methods,* 2005, Vol. 63, pp: 135-144). This primer was chosen because it has low specificity and binds at numerous loci within bacterial genomic DNA (gDNA).

Agarose gel (1%) electrophoresis of the PCR products provided a banding pattern (visible using a UV table) whereby duplicates of the same strain had the same banding pattern resulting in elimination of the duplicate from further study. Isolates that had unique banding patterns were included for further study.

Figure 4:
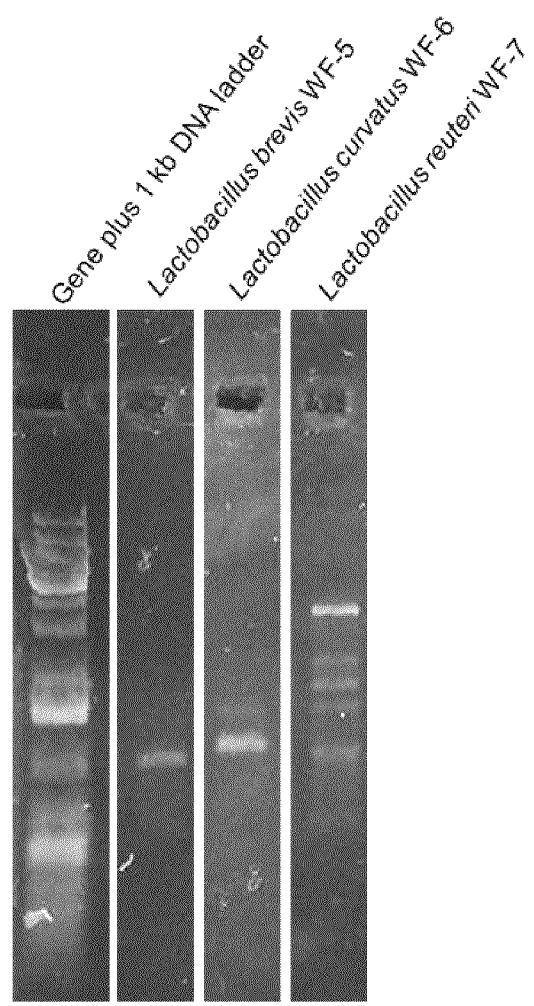
FIG. 4 shows the results of Random Amplified Polymorphic DNA (RAPD) polymerase chain reaction (PCR) profiling of *Lb. brevis* WF-5, *Lb. curvatus* WF-6, and *Lb. reuteri* WF-7.

FIG. 4 shows the RAPD profile of three of the seven isolates: *Lactobacillus brevis* WF-5, *Lactobacillus curvatus* WF-6, and *Lactobacillus reuteri* WF-7. The other isolates did not need RAPD profile identification because they either belong to different species or originate from a different wolf.

Isolate Identification by Whole Genome Sequencing (Illumina™ Sequencing)

To identify the selected isolates at the strain level, whole genome sequencing (Illumina™ Sequencing) was performed to get more detailed information of each strain. A Wizard™ Genomic DNA Purification Kit (Promega™) was used to isolate gDNA from each isolate. The concentration and quality of each gDNA sample was first determined using a Nanodrop™ spectrophotometer and further confirmed with 1% agarose gel electrophoresis. The qualified gDNA samples ($A_{260}/A_{280}$ was between 1.8 and 2.0; $A_{260}/A_{230}$ was over 2.0; Total yield was over 2,000 ng) were shipped to Quebec Genomics™ (Quebec, Quebec) for Illumina™ sequencing. Resulting sequences were analyzed with a serial of software. The adapter sequences were removed with Trimmomatic™ software, followed by sequence assembly with SPAdes™ software and assembly quality assessment with QUAST™ software. Scaffolding was done using Medusa™ web server.

Strain Deposit

The International Depository Authority of Canada (IDAC; 1015 Arlington Street, Winnipeg, Manitoba, Canada R3E 3R2) is a patent depository for microorganisms that has been made possible by Canada's accession to the Budapest Treaty on the International Recognition of the Deposit of Micro-Organisms for the Purposes of Patent Procedure (the Budapest Treaty) on Sep. 21, 1996.

Ten vials (0.5 mL each) of each isolate in frozen state (with 20% glycerol) were shipped in a Styrofoam™ box with dry ice to the IDAC in Winnipeg, Canada for deposit. The isolated strains were deposited on Dec. 18, 2018 and an accession number was assigned to each strain by the IDAC as listed in Table 1 above.

Example 3—Isolate Characterization

Whole Genome Sequence Analysis

Genome annotation was done by uploading a FASTA file of contigs onto the RAST (Rapid Annotation using Subsystem Technology) server and a detailed annotation report of each strain was generated. Bioinformatics software (e.g. Geneious™) and online databases and tools (e.g. via the National Center for Biotechnology Information website) were used to identify the presence or absence of specific functioning genes (e.g. bacteriocin encoding genes, host adhesion factors, and bile salt tolerance genes), virulence genes, and antibiotic resistance genes, and determine whether certain antibiotic resistance genes are transferable or not. Table 3 shows the results of whole genome sequence analysis of the seven isolates.

TABLE 3

| Descriptions | Seven Wolf Isolates | | | | | | |
| --- | --- | --- | --- | --- | --- | --- | --- |
| | WF-1 | WF-2 | WF-3 | WF-4 | WF-5 | WF-6 | WF-7 |
| Possibly missing genes | 13 | 32 | 10 | 15 | 19 | 11 | 16 |
| Size (bp) | 2,087,568 | 2,343,220 | 2,579,333 | 3,353,275 | 2,742,948 | 2,158,826 | 2,087,104 |
| GC content (%) | 38.5 | 40.7 | 37.9 | 44.3 | 45.3 | 41.6 | 38.5 |
| N50 | 62,149 | 202,488 | 131,451 | 463,326 | 354,899 | 246,690 | 61,073 |
| L50 | 12 | 5 | 6 | 3 | 4 | 3 | 13 |
| # of contigs (with PEGs) | 70 | 37 | 39 | 44 | 38 | 20 | 71 |
| # of scaffolds | 11 | 19 | 5 | 15 | 12 | 2 | 11 |
| # of subsystems | 307 | 307 | 341 | 334 | 316 | 303 | 307 |
| # of coding sequences | 1,989 | 2,121 | 2,510 | 3,140 | 2,665 | 2,088 | 1,986 |
| # of RNAs | 72 | 64 | 68 | 77 | 71 | 61 | 72 |
| # of adhesion genes | 2 | 2 | 1 | 2 | 2 | 2 | 2 |
| # of toxins and superantigens | 0 | 0 | 0 | 0 | 0 | 0 | 0 |
| # of bacteriocins, ribosomally synthesized antibacterial peptides | 0 | 0 | 7 | 0 | 0 | 7 | 0 |
| # of copper homeostasis genes | 3 | 5 | 7 | 6 | 6 | 6 | 3 |
| # of bile hydrolysis genes | 1 | 1 | 2 | 3 | 4 | 1 | 1 |

Growth Curve Generation

To assess the growth dynamics of each strain, a 96-well micro titer plate was used for bacteria cultivation and the optical density at 600 nm of each well containing 200 µL of fluid was monitored with a multipurpose plate reader (Varioskan™) every two hours. For each strain, 1% fully-grown culture (2 µL) was sub-cultured into 198 µL of MRS broth and incubated at 37° C. for 60 hours. Four strains, *Lb. fermentum* ATCC 14931, *Lb. reuteri* ATCC 23272, *Lb. casei* K9-1, and *Lb. fermentum* K9-2, were included as controls. One well containing 200 µL of MRS broth only was used as a sterility control. All tests were done in triplicate.

Figure 5:
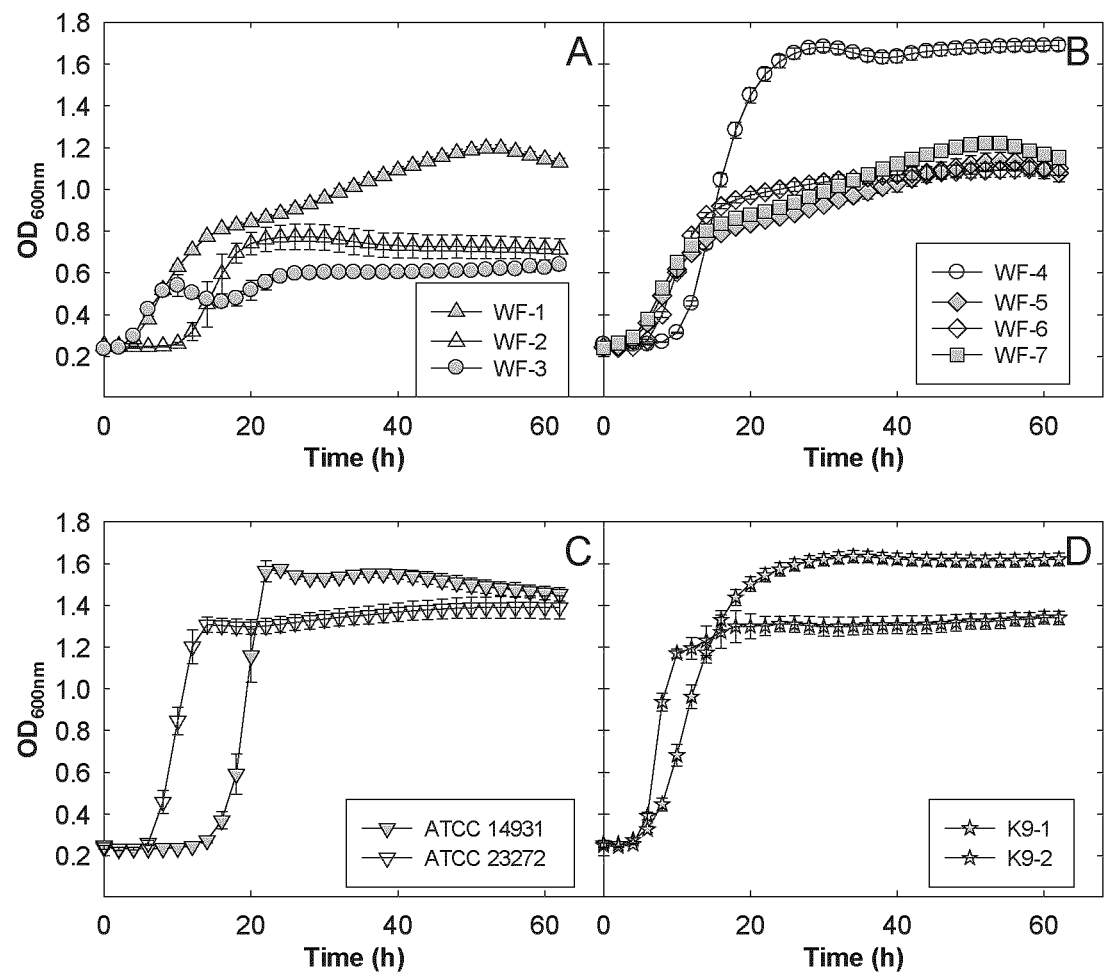
FIG. 5 shows growth curves for *Lb. reuteri* WF-1, *Lb. animalis* WF-2, and *Ec. faecium* WF-3 (panel A); *Lb. plantarum* WF-4, *Lb. brevis* WF-5, *Lb. curvatus* WF-6, and *Lb. reuteri* WF-7 (panel B); ATCC 14931 and ATCC 23272 (panel C); and K9-1 and K9-2 (panel D)

Optical densities of each strain were plotted as a function of time, which was defined as the growth curve of each strain. The growth curves of the seven wolf isolates and controls are shown in FIG. 5. It took about 24 h for all strains to reach late exponential or early stationary growth phase.

Auto-Aggregation Ability

Figure 6:
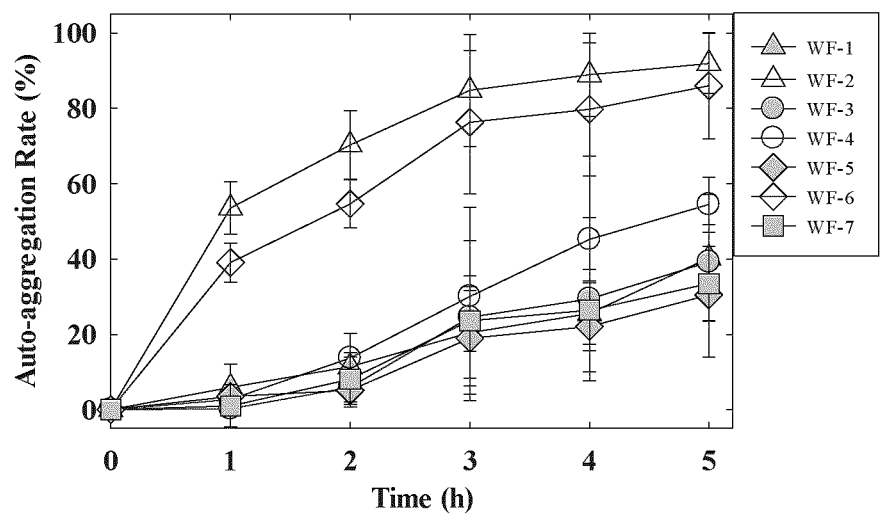
FIG. 6 shows auto-aggregation assay results for the seven isolated strains of FIG. 1.

To assess the auto-aggregation ability of the isolates, auto-aggregation assays were performed. For each isolate, 30 mL of fully-grown culture was mixed thoroughly by vortexing. The initial optical density at 600 nm ($OD_{600}$, $A_0$) was measured and recorded. The remaining cell suspension was kept still and undisturbed at ambient temperature for 5 hours. One hundred µL of the upper suspension (the cell suspension was not vortexed) was taken at one-hour intervals to measure the $OD_{600\ nm}$ ($A_t$). The auto-aggregation percentage was expressed as:

$$1 - \frac{A_t}{A_0}$$

wherein $A_0$ stands for $OD_{600}$ at 0 h, and $A_t$ stands for $OD_{600}$ at 1 h, 2 h, 3 h, 4 h, or 5 h. The auto-aggregation rates (in percentage) of the seven wolf isolates are shown in FIG. 6.

Cell Surface Hydrophobicity

To assess the hydrophobic nature of the bacterial cell surface of each isolate, microbial adhesion to hydrocarbons (MATH) assays (Otero et al. "Bacterial surface characteristics applied to selection of probiotic microorganisms", in *Public Health Microbiology* 2004, pp. 435-440. Humana Press) were performed to measure the hydrophobicity of bacterial strains in terms of adhesion. For each isolate, 10 mL of fully-grown culture was harvested by centrifugation at 8,000 rpm for two minutes, followed by washing the cells with saline solution three times. The cell pellet was resuspended with saline solution and the $OD_{600}$ of each cell suspension was adjusted to 0.5±0.1. The actual final $OD_{600}$ of each cell suspension was measured and recorded. Three point six mL of cell suspension was aliquoted to a glass testing tube, followed by aliquoting 0.6 mL of solvent (toluene or xylene) to the same glass testing tube and vortexing vigorously for 1 minute. The testing tube was kept still for 1 hour to allow the immiscible solvent and aqueous phase to separate. The aqueous layer was removed with a Pasteur pipet and the $OD_{600}$ ($OD_{test}$) was measured and recorded. The percentage of hydrophobicity of each strain was calculated as the following formula:

% hydrophobicity=$(OD_{initial}-OD_{test})/OD_{initial}$

Figure 7:
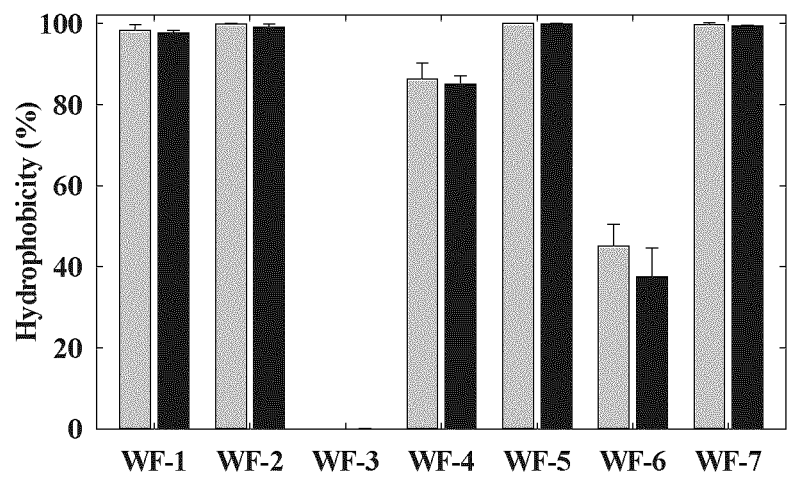
FIG. 7 shows cell surface hydrophobicity assay results for the seven isolated strains of FIG. 1.

The percentage hydrophobicities of the seven isolates are shown in FIG. 7.

Low pH and Bile Salt Tolerance Assays

To assess the tolerance of the isolates to acidic conditions, for each isolate, 1% of fully-grown culture (10 µL) was subcultured into a set of 1 mL solutions of Simulated Gastric Fluid (SGF, without pepsin) with varying pH values (pH=2.0, 2.5, 3.0, and 6.9). The SGF solutions with different pH values were prepared by adjusting the pH of SGF with HCl and NaOH, followed by sterilization by filtering. Once a culture was inoculated into each SGF solution, the mixture was mixed thoroughly by vortexing and 60 µL of each mixture was aliquoted into the first column of a 96-well microtiter plate right away for diluting and plating. The remaining cultures were immediately incubated at 37° C. under airtight conditions for 6 h. Sixty µL of each culture was aliquoted into the first column of a new 96-well microtiter plate after 2 h, 4 h, and 6 h, respectively, for diluting and plating.

To assess the tolerance of the isolates to bile salt, for each isolate, 1% fully-grown culture (10 µL) was subcultured into a set of 1 mL of Phosphate Buffered Saline (PBS, pH=7.2) with varying bile salt concentrations (0%, 3%, and 5%). The PBS solutions with different bile salt concentrations were prepared by dissolving a corresponding amount of bile salt into sterile PBS. Once a culture was inoculated into each PBS solution, the mixture was mixed thoroughly by vortexing and 60 µL of each mixture was aliquoted into the first column of a 96-well microtiter plate right away for diluting and plating. The remaining cultures were immediately incubated at 37° C. under airtight conditions for 24 h. Sixty µL of each culture was aliquoted into the first column of a new 96-well microtiter plate after 6 h and 24 h, respectively, for diluting and plating.

Figure 8:
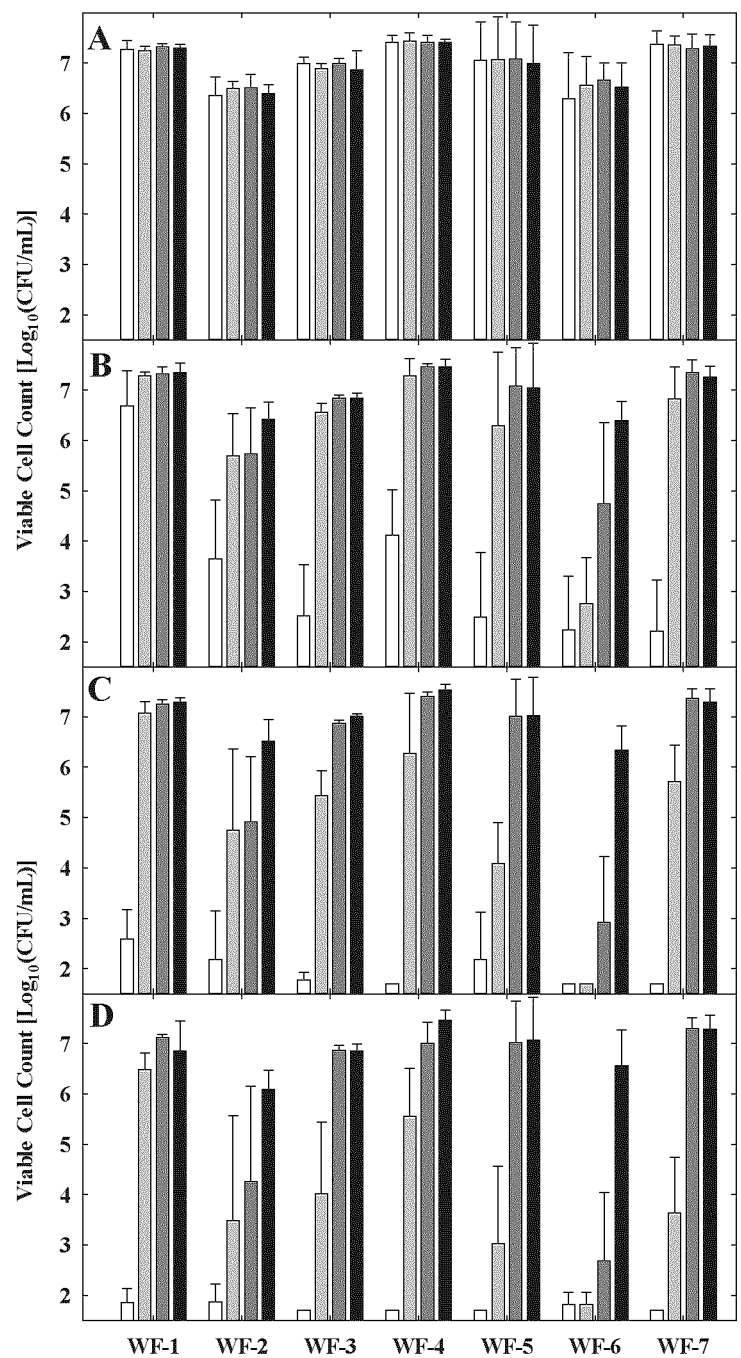
FIG. 8 shows low pH tolerance assay results for the seven isolated strains of FIG. 1 (panel A: t=0; panel B: t=2 h; panel C: t=4 h; panel D: t=6 h; white bar: pH=2.0; light grey bar: pH=2.5; dark grey bar: pH=3.0; black bar: pH=6.9)
Figure 9:
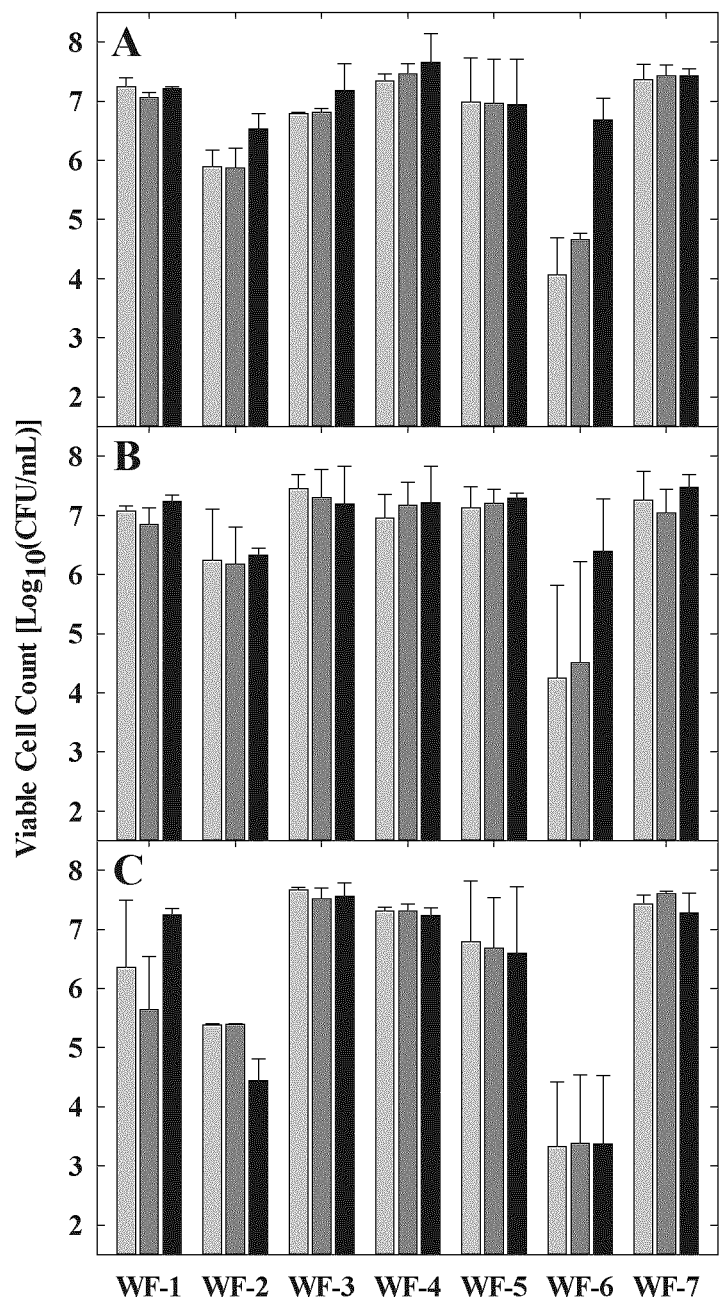
FIG. 9 shows bile salt tolerance assay results for the seven isolated strains of FIG. 1 (panel A: t=0; panel B: t=6 h; panel C: t=24 h; light grey bar: 5% bile salt; dark grey bar: 3% bile salt; black bar: 0% bile salt)

A serial 10-fold dilution of each culture was prepared and proper dilutions were plated on MRS agar plates and incubated at 37° C. for 2 days. Viable cell counts were recorded and expressed as the Mean [$\log_{10}$(CFU/mL)]±Standard Error of at least three independent replicates. The results of the low pH and bile salt tolerance assays for the seven isolates are shown in FIGS. 8 and 9, respectively.

Gastric and Intestinal Digestive Enzyme Tolerance Assays

To assess the tolerance of the isolates to gastric digestive enzyme, for each isolate, 1% fully-grown culture (10 µL) was subcultured into a set of 1 mL of SGF solutions (with 3.2 mg/mL of pepsin) with varying pH values (pH=2.0, 2.5, and 3.0). The cultures were incubated at 37° C. under airtight conditions for 6 h. Sixty µL of each culture was aliquoted into the first column of a 96-well microtiter plate after 0 h, 2 h, 4 h, and 6 h, respectively, for diluting and plating.

To assess the tolerance of the isolates to intestinal digestive enzyme, for each isolate, 1% fully-grown culture (10 µL) was subcultured into a set of 1 mL of Simulated Intestinal Fluid (SIF) solutions with 10 mg/mL of pancreatin at pH=6.8. The cultures were incubated at 37° C. under airtight conditions for 24 h. Sixty µL of each culture was aliquoted into the first column of a 96-well microtiter plate after 0 h, 6 h, and 24 h, respectively, for diluting and plating.

Figure 10:
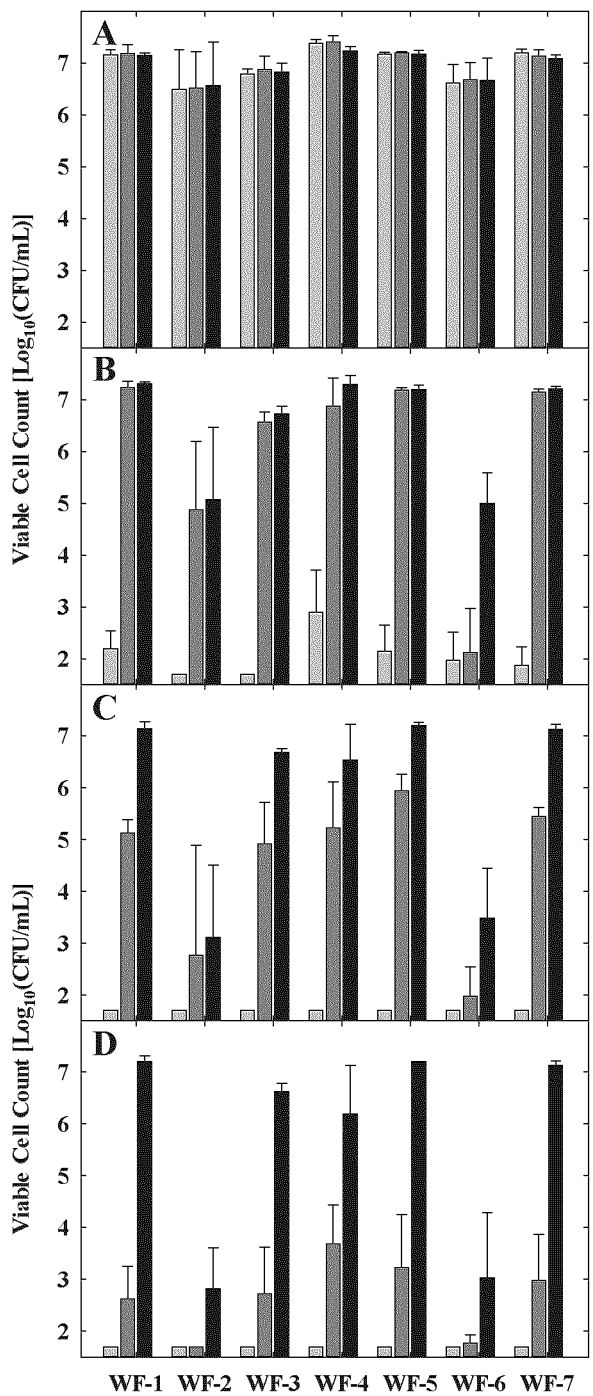
FIG. 10 shows gastric digestive enzyme (3.2 mg/mL pepsin) tolerance assay results for the seven isolated strains of FIG. 1 (panel A: t=0; panel B: t=2 h; panel C: t=4 h; panel D: t=6 h; light grey bar: pH=2.0; dark grey bar: pH=2.5; black bar: pH=3.0)
Figure 11:
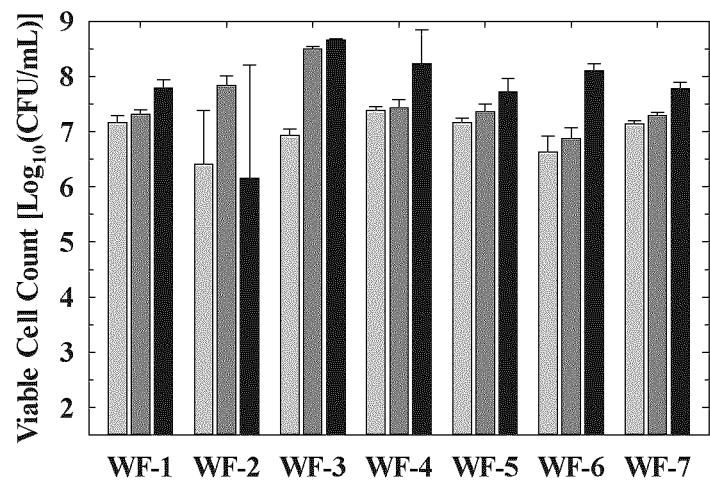
FIG. 11 shows intestinal digestive enzyme (10 mg/mL pancreatin) tolerance assay results for the seven isolated strains of FIG. 1 (light grey bar: t=0; dark grey bar: t=6 h; black bar: t=24 h)

A serial 10-fold dilution of each culture was prepared and proper dilutions were plated on MRS agar plates and incubated at 37° C. for 2 days. Viable cell counts were recorded and expressed as the Mean [$\log_{10}$(CFU/mL)]±Standard Error of at least three independent replicates. The results of the gastric digestive enzyme and intestinal digestive enzyme tolerance assays for the seven isolates are shown in FIGS. 10 and 11, respectively.

Production of Inhibitory Substances

To assess the ability of the isolates to produce any inhibitory substances against a series of pathogens and spoilage microorganisms, the isolates were grown in the presence of a series of indicator strains. For each isolate, 1 µL of fully-grown culture was spotted on Reinforced Clostridial Agar (RCA) plates and incubated at 37° C. overnight. Fourteen non-LAB indicator strains were cultivated in Trypticase Soy Broth with 0.6% Yeast Extract (TSBYE) at 37° C. overnight. Each indicator strain (0.1%, 6 µL) was inoculated into 6 mL of RCA soft agar (with 0.75% agar) and solidified agar plates were incubated at 37° C. overnight. *Lactococcus lactis* ATCC 11454 and *Enterococcus faecalis* 710C were used as control strains that produce inhibitory substances against Gram-negative and Gram-positive bacteria, respectively. The inhibitory zone size without visible growth of indicator strains was measured and recorded.

The results for the seven isolates are shown in Table 4. In Table 4: "Yes" indicates that an isolate produces inhibitory substances against the corresponding indicator strain; "No" indicates that the strain does not produce inhibitory substances against the corresponding indicator strain; and "n/a" means not applicable.

determine the antibiotic susceptibility of all isolates against eight commonly used clinical antibiotics. A variety of enterococcal and non-enterococcal control strains were also tested as listed in Tables 5 and 6 below.

Broth micro-dilution for non-enterococcal lactic acid bacteria was performed following the methods according to: International Organization for Standardization, *Milk and milk products—Determination of the minimal inhibitory concentration (MIC) of antibiotics applicable to bifidobacteria and non-enterrococcal lactic acid bacteria (LAB)* (ISO 10932:2012). Broth micro-dilution for enterococcal bacteria was performed following the methods according to: CLSI, *Methods for Dilution Antimicrobial Susceptibility Tests for Bacteria that Grow Aerobically,* 9$^{th}$ edition, CLSI standard M07, Wayne, Pa.: Clinical and Laboratory Standards Institute; 2012. Disk diffusion methods for all bacteria were performed following the methods according to: CLSI, *Performance Standards for Antimicrobial Disk Susceptibility Tests,* 11$^{th}$ edition, CLSI Standard M02, Wayne, Pa.: Clinical and Laboratory Standards Institute; 2012. Antibiotic stock solutions were prepared following the methods according to: CLSI, *Performance Standards for Antimicrobial Susceptibility Testing,* 23$^{rd}$ edition, CLSI Standard M100, Wayne, Pa.: Clinical and Laboratory Standards Institute; 2013.

The results of the antibiotic susceptibility assays for the seven isolates are shown in Table 5. In Table 5: AMP=Ampicillin; GEN=Gentamycin; KAN=Kanamycin; STR=streptomycin; ERY=erythromycin; CLI=Clindamycin; TET=Tetracycline;

TABLE 4

| | Wolf Isolates | | | | | | | Control Strains | |
| | | | | | | | | *L. lactis* | *E. faecalis* |
| Indicator Strains | WF-1 | WF-2 | WF-3 | WF-4 | WF-5 | WF-6 | WF-7 | ATCC 11454 | 710C |
|---|---|---|---|---|---|---|---|---|---|
| *E. coli* ATCC 11775 | Yes | Yes | Yes | Yes | Yes | Yes | Yes | Yes | n.a. |
| *E. coli* ATCC 43895 | Yes | Yes | Yes | Yes | Yes | Yes | Yes | Yes | n.a. |
| *S. enteric* ATCC 13311 | Yes | Yes | Yes | Yes | Yes | Yes | Yes | Yes | n.a. |
| *S. enteric* ATCC 8326 | Yes | Yes | Yes | Yes | Yes | No | Yes | Yes | n.a. |
| *L. monocytogenes* ATCC 19116 | Yes | Yes | Yes | Yes | Yes | Yes | Yes | n.a. | Yes |
| *L. monocytogenes* ATCC 43256 | No | Yes | Yes | Yes | No | No | Yes | n.a. | Yes |
| *S. aureus* R667 | Yes | Yes | Yes | Yes | Yes | Yes | Yes | n.a. | Yes |
| *S. aureus* R776 | Yes | Yes | Yes | Yes | Yes | Yes | Yes | n.a. | Yes |
| *E. faecium* R704 | Yes | Yes | Yes | Yes | Yes | No | Yes | n.a. | Yes |
| *E. faecium* R846 | Yes | Yes | Yes | Yes | Yes | No | Yes | n.a. | Yes |
| *C. perfringens* NCTC 8533 | Yes | Yes | Yes | Yes | Yes | Yes | Yes | n.a. | Yes |
| *C. perfringens* 15 | Yes | Yes | Yes | Yes | Yes | Yes | Yes | n.a. | Yes |
| *C. difficile* 293 | Yes | Yes | Yes | Yes | Yes | Yes | Yes | n.a. | Yes |
| *C. difficile* 54 | Yes | Yes | Yes | Yes | Yes | Yes | Yes | n.a. | Yes |

Antibiotic Susceptibility Assay

To assess the antibiotic susceptibility of all isolates, broth microdilution and disk diffusion methods were used to CHL=chloramphenicol; and "R" indicates resistance to a given antibiotic, meaning that the MIC is above the highest concentration tested (n≥2).

TABLE 5

| MIC (µg/mL) | AMP | GEN | KAN | STR | ERY | CLI | TET | CHL |
|---|---|---|---|---|---|---|---|---|
| *E. coli* ATCC 25922 | 2 | 0.5 | 3 | 4 | R | R | 0.5 | 4 |
| *P. aeruginosa* ATCC 27853 | 0.063 | 0.5 | 3 | 8 | 0.013 | 0.063 | 0.125 | 4 |
| *S. aureus* ATCC 25923 | R | 1 | 1024 | R | R | R | 8 | R |
| *E. faecium* WF-3 | 1 | 32 | 512 | 64 | 4 | 0.25 | 64 | 8 |
| *L. casei* K9-1 | 0.75 | 4 | 64 | 32 | 0.375 | 6 | 2 | 12 |
| *L. fermentum* K9-2 | 0.313 | 3.5 | 64 | 40 | 0.5 | 0.094 | 6 | 6 |

TABLE 5-continued

| MIC (µg/mL) | AMP | GEN | KAN | STR | ERY | CLI | TET | CHL |
|---|---|---|---|---|---|---|---|---|
| L. fermentum ATCC 14931 | 0.25 | 12 | 384 | 170.7 | 0.375 | 0.047 | 6 | 5 |
| L. reuteri ATCC 23272 | 1 | 4 | 192 | 64 | 1 | 0.063 | 32 | 8 |
| L. lactis ATCC 11454 | 0.625 | 20 | 144 | 128 | 0.5 | 4.125 | 8.125 | 6 |
| L. reuteri WF-1 | 2 | 14 | 320 | 64 | 1 | 16 | 32 | 8 |
| L. animalis WF-2 | 2 | 96 | 1024 | 256 | 0.5 | 2 | 4 | 8 |
| L. plantarum WF-4 | 0.75 | 28 | 256 | 160 | 0.5 | 8 | 16 | 8 |
| L. brevis WF-5 | 4 | 12 | 192 | 96 | 0.75 | R | 16 | 8 |
| L. curvatus WF-6 | 2 | 48 | 96 | 256 | 1 | 16 | 16 | 8 |
| L. reuteri WF-7 | 2 | 17.5 | 80 | 144 | 1 | 16 | 32 | 8 |

Table 6 shows the results of antimicrobial susceptibility tests using BD BBL™ Sensi-Disc™ Antimicrobial Susceptibility Test Discs with a diameter of 6 mm (n≥2). Note that in Table 6, AMP=Ampicillin; GEN=Gentamycin; KAN=Kanamycin; STR=streptomycin; ERY=erythromycin; CLI=Clindamycin; TET=Tetracycline; CHL=chloramphenicol.

TABLE 6

| MIC (mm) | AMP (10 µg) | GEN (10 µg) | KAN (30 µg) | STR (10 µg) | ERY (15 µg) | CLI (2 µg) | TET (30 µg) | CHL (30 µg) |
|---|---|---|---|---|---|---|---|---|
| E. coli ATCC 25922 | 20 | 22 | 23 | 18 | 0 | 0 | 25 | 24 |
| P. aeruginosa ATCC 27853 | 0 | 17 | 0 | 7 | 0 | 0 | 14 | 0 |
| S. aureus ATCC 25923 | 32 | 22 | 22 | 14 | 26 | 24 | 28 | 23 |
| E. faecium WF-3 | 22 | 14 | 13 | 7 | 17 | 24 | 0 | 25 |
| L. casei K9-1 | 45 | 29 | 18 | 21 | 50 | 22 | 45 | 36 |
| L. fermentum K9-2 | 35 | 24 | 18 | 17 | 36 | 36 | 28 | 31 |
| L. fermentum ATCC 14931 | 44 | 21 | 9 | 10 | 40 | 42 | 26 | 35 |
| L. reuteri ATCC 23272 | 38 | 17 | 10 | 10 | 27 | 33 | 22 | 29 |
| L. lactis ATCC 11454 | 30 | 20 | 11 | 10 | 33 | 10 | 20 | 30 |
| L. reuteri WF-1 | 23 | 23 | 15 | 12 | 33 | 0 | 17 | 28 |
| L. animalis WF-2 | 26 | 15 | 0 | 7 | 34 | 28 | 34 | 30 |
| L. plantarum WF-4 | 30 | 20 | 11 | 10 | 32 | 10 | 19 | 29 |
| L. brevis WF-5 | 28 | 20 | 11 | 11 | 33 | 8 | 19 | 29 |
| L. curvatus WF-6 | 36 | 16 | 16 | 4 | 40 | 35 | 30 | 32 |
| L. reuteri WF-7 | 20 | 22 | 15 | 12 | 32 | 0 | 15 | 27 |

Cell Binding Assay

To assess the adhesion ability of isolates in vitro, two canine cell lines, MDCK and DH82, were used in this study. Canis familiaris ATCC CCL-34 (MDCK (NBL-2)) and Canis familiaris ATCC CRL-10389 (DH82) and were resuscitated from frozen stocks stored in a liquid nitrogen tank with a complete medium in a tissue culture flask. The base medium used in this study for cell line cultivation was DMEM (Dubecco's Modified Eagle Media; Gibco™) with high glucose level, glutamine, and sodium pyruvate. The complete medium was composed of DMEM and 10% heat-inactivated (56° C. for 30 min) fetal bovine serum (FBS; Gibco™). The growth condition was 37° C. with 5% $CO_2$. The solution used for cell dispersion was 0.25% (w/v) Trypsin with 0.53 mM EDTA (ethylenediaminetetraacetic acid). The cell line cultures were maintained for two weeks after the confluence to allow full differentiation before the adhesion assay. A hemocytometer was used for cell counting.

Bacterial cell suspensions were prepared by harvesting 5 mL of fully-grown culture by centrifugation at 3,500 g for 10 min, followed by washing cells with PBS (pH=7.4) three times. The cell pellet was resuspended in base medium DMEM and adjusted to an $OD_{600\ nm}$ of around 1.0 for the seven wolf isolates and around 0.1 for control strains L. monocytogenes ATCC 19116 and S. enterica ATCC 13311 which corresponds to about $5\times10^8$ CFU/mL for the wolf isolates and about $1\times10^8$ CFU/mL for the control strains.

Cell monolayers of MDCK and DH82 cells were prepared in 12-well tissue culture plates. Cells were inoculated at a concentration of $4\times10^4$ cells per well to obtain confluence and allowed to differentiate. The culture medium was changed every two days. Once the cells were confluent, the complete medium was removed followed by washing cells with PBS for three times. One mL of base medium DMEM was added to each well and incubated at 37° C. with 5% $CO_2$ for 1 h before the adhesion assay.

For each strain, a 1 mL aliquot of bacterial cell suspension was added to the confluent monolayer cells and incubated at 37° C. with a 5% $CO_2$ atmosphere for 2 h. One mL of base medium DMEM was added to one well to serve as a sterility control. Two hours later, the monolayer cells were washed with PBS for three times. Two hundred fifty µL of Trypsin-EDTA solution was added to each well until cell layer was dispersed, followed by adding 1.75 mL of complete medium and aspirating cells by pipetting. Each cell suspension was divided into two portions: one for evaluation of in vitro adhesion and the other for cytokine profiling by RT-qPCR as described in more detail below. The cell suspensions were kept at −80° C. until further analysis. Note that the control strains of L. monocytogenes and S. enterica were only used for cytokine profiling and not for evaluation of in vitro adhesion.

Figure 12:
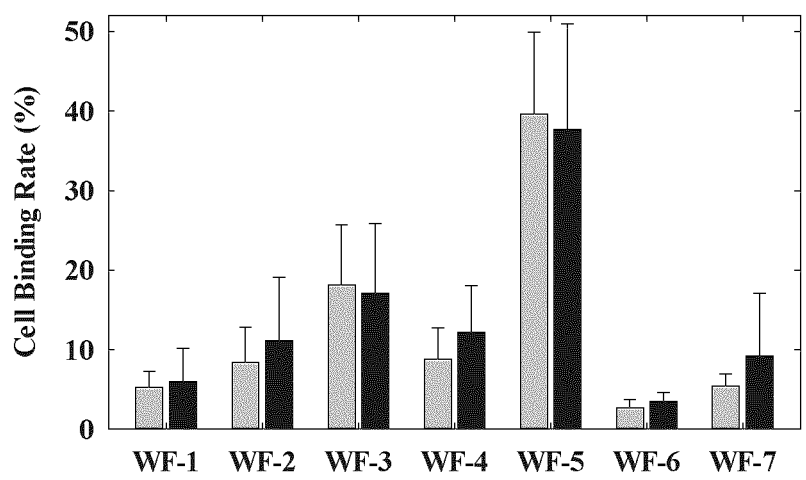
FIG. 12 shows cell binding assay results for the seven isolated strains of FIG. 1 (grey bar: MDCK cells; black bar: DH82 cells)

A serial 10-fold dilution of each culture was prepared and proper dilutions were plated on MRS agar plates and incubated at 37° C. for 2 days. Viable cell counts were recorded and expressed as the Mean [$\log_{10}$(CFU/mL)]±Standard Error of at least three independent replicates. The cell binding rate for each isolate was calculated as the viable cell count that bound to cell lines over the original inoculated CFU of the bacterial cell suspensions to the cell line. The results of the cell binding assays are shown in FIG. 12.

Cytokine Profiling

To assess the ability of the isolates to alter the expression of a series of cytokines in canine-originated cell lines, RT-qPCR was performed to evaluate the cytokine expression change at the gene level.

The primers used in the RT-qPCR experiments are listed in Table 7. In Table 7: IL=interleukin; IFN=interferon; TFG=transforming growth factor; TNF=tumor necrosis factor; GADPH=glyceraldehyde 3-phosphate dehydrogenase; Th1=T helper cell type 1; Th2=T helper cell type 2; F=forward primer; R=reverse primer; N/A=not applicable.

TABLE 7

| Cytokine | Cell Type | Primer Sequence | Primer SEQ ID NO: | Amplicon size (bp) | Position |
|---|---|---|---|---|---|
| IL-4 | Th2 | F: CTCACCAGCACCTTTGTCCA | 11 | 207 | 20972804 to |
|  |  | R: CTCCTTGTCCGTCACCAACC | 12 |  | 20973010 |
| IL-6 | Th2 | F: GCACTGAGAAAGGAGGTGGG | 13 | 204 | 36474669 to |
|  |  | R: CCTGAGACCAGCAGCAGAAA | 14 |  | 36474872 |
| IL-10 | Th1/Th2 | F: AACCCCTCCCTTCTCAAACT | 15 | 243 | 5937243 to |
|  |  | R: TAGAACCCACAACTGCTGGC | 16 |  | 5937485 |
| IL-12A | Th1 | F: GGGGAAAGGATGCCCCAA | 17 | 200 | 26133619 to |
|  |  | R: ACGGAGCTGTGGTTAATGGG | 18 |  | 26133818 |
| IL-12B | Th1 | F: CCTGACTGGTGGATGTGACC | 19 | 217 | 51194483 to |
|  |  | R: GCAGTCCTGGTAAATGTGGGA | 20 |  | 51194699 |
| IFN-γ | Th1 | F: CATCTCCTTCTGCTGCTGGT | 21 | 224 | 10411729 to |
|  |  | R: ACAAGAATGGCACAGAGGGG | 22 |  | 10411952 |
| TGF-β1 | Th2 | F: TCATTCGTTTCCTCCCACCG | 23 | 212 | 112643985 to 112644196 |
|  |  | R: ATCTCTCTGGGCTCTGGCTT | 24 |  |  |
| TNF-α | Th1 | F: GCCAGTAGCTCATGTTGTAGG | 25 | 249 | 1075533 to |
|  |  | R: TGGCCCTCGGGTTCTG | 26 |  | 1075781 |
| GAPDH | N/A | F: GGATTAAGTTGGGGCAGGGA | 27 | 230 | 38468833 to |
|  |  | R: AAAGCAGTTGGGAGTCTGGC | 28 |  | 38469062 |

Bacterial cell suspensions were collected as described above for the cell binding assay and included suspensions of control strains of L. monocytogenes and S. enterica. The cell suspensions were used to isolate total RNA using a Qiagen™ RNeasy™ Mini Kit, followed by concentration and quality check using a Nanodrop™ spectrophotometer. RNA samples were kept at −80° C. for further analysis.

The mRNA in the RNA samples was reverse transcribed into cDNA using a Qiagen™ QuantiTect™ Reverse Transcription Kit, followed by concentration and quality check using a Nanodrop™ spectrophotometer. The cDNA samples were kept at −80° C. for further analysis.

Each PCR reaction mixture had a total volume of 25 μL containing 12.5 μL of 2× Master Mix, 1.5 μL of cDNA, and 1 μL of forward and 1 μL of reverse primers (10 μM) as listed in Table 4. In total nine pairs of primers, including 8 cytokines (IL-4, IL-6, IL-10, IL-12a, IL-12β, IFN-γ, TGF-β1, and TNF-α) and one endogenous control (GAPDH), were tested.

Figure 13:
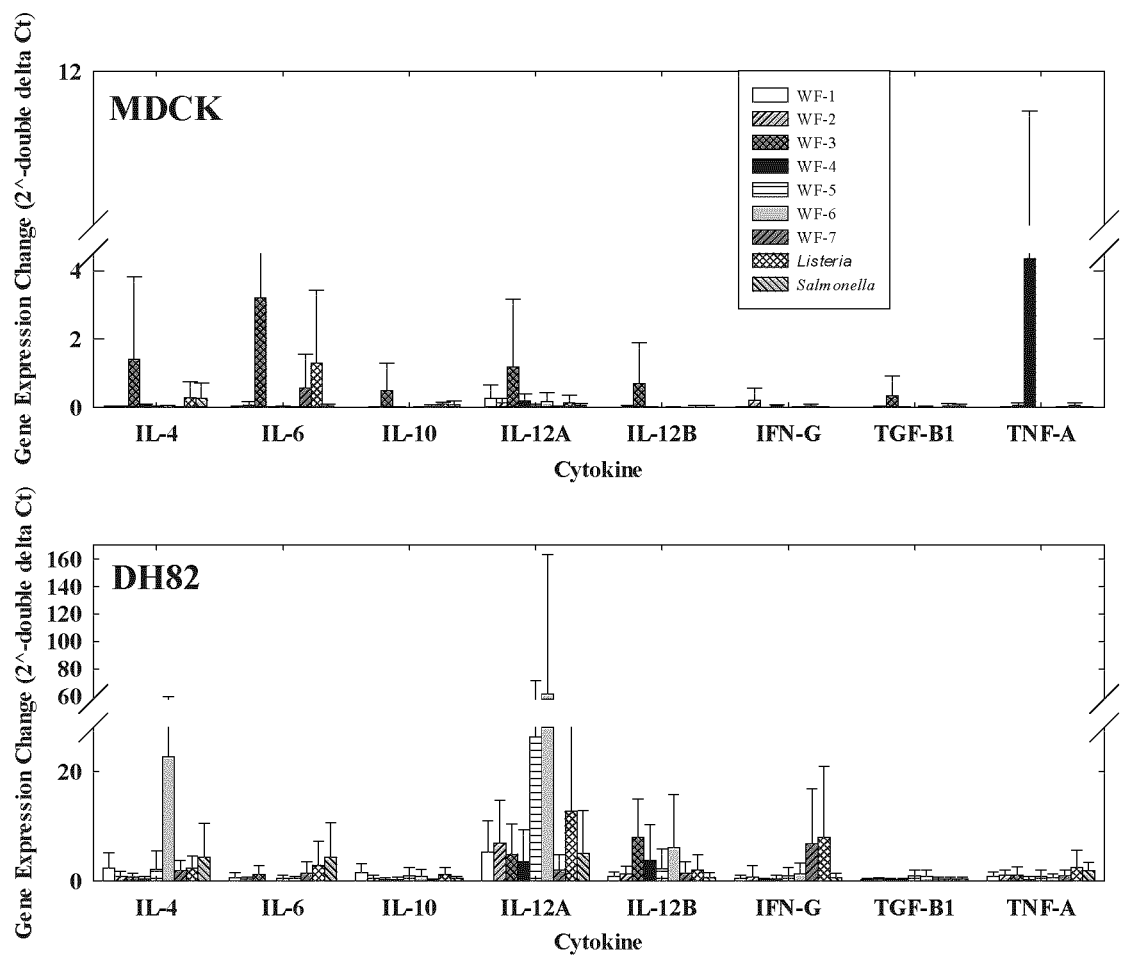
FIG. 13 shows cytokine profiling results for the seven isolated strains of FIG. 1 by RT-qPCR in two canine cell lines (top panel: MDCK cells; bottom panel: DH82 cells)

The qPCR data were normalized in each individual sample using the level of GAPDH expression. Gene expression was measured by the comparative cycle threshold method ($\Delta\Delta C_T$) and was reported as the n-fold (n-fold= $2^{-\Delta\Delta C_T}$) difference relative to the normalized expression of reference samples (cDNA preparations made from control samples). Comparisons between the n-fold values of the two groups were performed using the t-Student test. Significance was taken at P<0.05. The results of the RT-qPCR experiments are shown in FIG. 13.

Example 4—Shelf Life Stability Studies

Shelf Life of Freeze-Dried Forms of Isolated Strains

Figure 14:
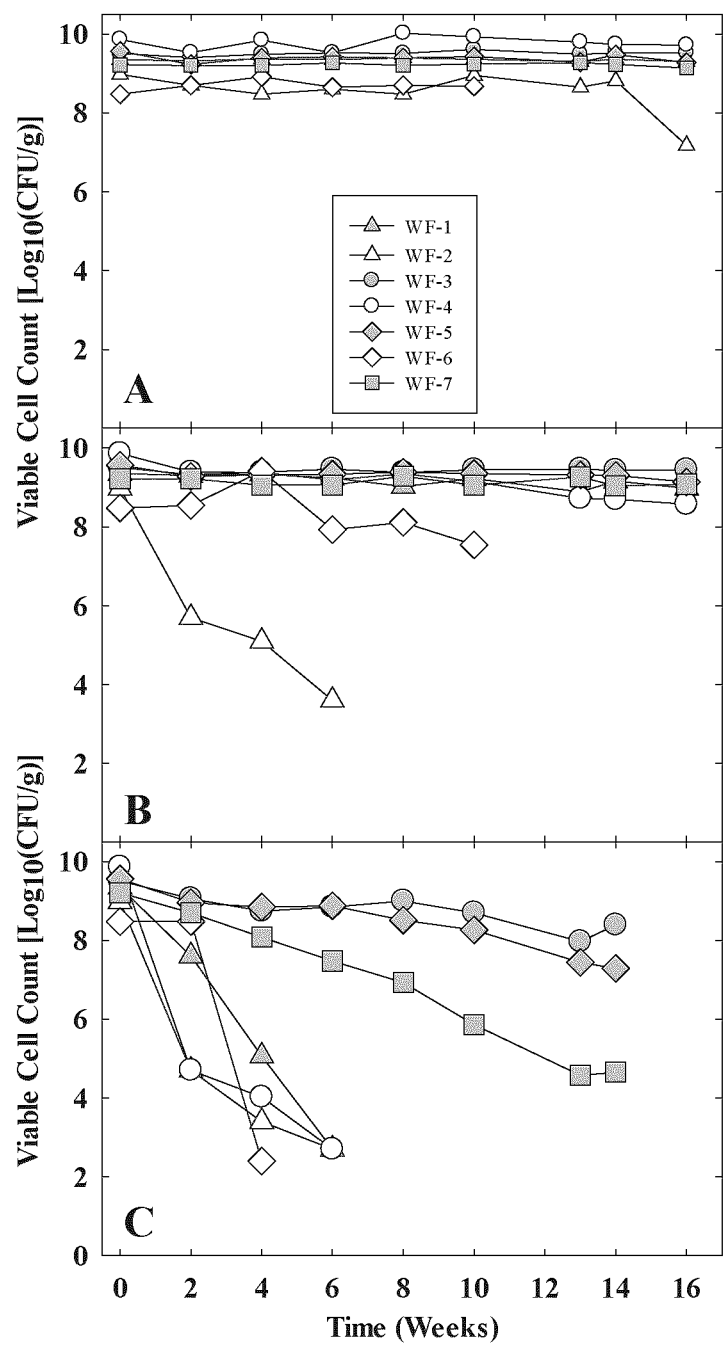
FIG. 14 shows shelf-life stability results for freeze-dried forms of the seven isolated strains of FIG. 1 at 4° C. (panel A), 25° C. (panel B), and 37° C. (panel C)

To assess the strain stability of the isolates, and thereby their potential shelf life, 800 mL of fully-grown culture of each strain was freeze-dried using 10% (w/v) maltodextrin as a cryoprotectant in a LyoStar™ II lyophilizer. The freeze-dried products were divided into three portions, one stored at 4° C., one at 25° C., and one at 37° C., for up to 16 weeks. The viability of each sample was tested every two weeks. The results of the shelf life studies of the freeze-dried products are shown in FIG. 14.

Shelf Life of Freeze-Dried Forms of Isolated Strains Incorporated into Dog Food

Figure 15:
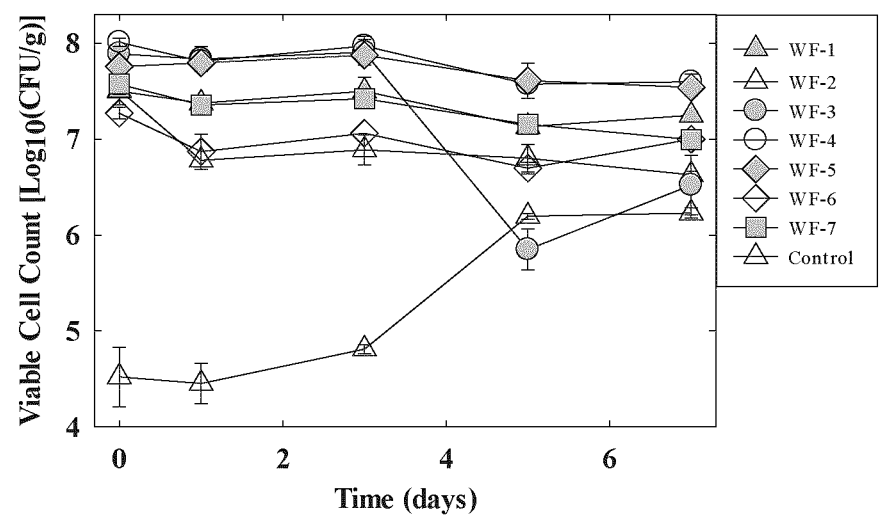
FIG. 15 shows shelf-life stability results for freeze-dried forms of the seven isolated strains of FIG. 1, incorporated into raw and frozen dog food at 4° C.

The freeze-dried products were also incorporated into a commercial frozen raw dog diet (BEEF & TRIPE COMPLETE FOR DOGS, Red Dog Blue Kat™, Vancouver, BC, Canada) a 2% inclusion rate and then stored under conditions mimicking commercial production and storage conditions. Briefly speaking, 1 g of freeze-dried product was added to a portion of 50 g of dog diet, followed by mixing thoroughly by massaging and then distributing the product into five sterile stomaching bags. A first bag was sampled for viable cell count immediately (Day 0). The remaining samples were vacuum-packaged and stored at −20° C. for more than one week. A second bag was then withdrawn and kept refrigerated for seven days (Day 7). Two days later, a third bag of sample was withdrawn and kept refrigerated for five days (Day 5). Two days after that, a fourth bag was withdrawn and kept refrigerated for three days (Day 3) and, a fifth bag was withdrawn and kept refrigerated for one day (Day 1). One set of samples without the addition of any isolates were included to monitor the change of background microflora. The results of the shelf life studies of the freeze-dried products incorporated into frozen raw dog diet are shown in FIG. 15.

Example 5—Summary of Results of Examples 3 and 4

All seven strains were whole genome sequenced. Based on whole genome sequence analysis, all seven strains are free of genes coding for toxins and superantigens. They all have bile hydrolysis genes and adhesion genes. WF-3 and WF-6 have genes coding for bacteriocins or antibacterial peptides.

WF-2 and WF-6 showed the high auto-aggregation rate, over 80% for WF-2 and 75% for WF-6 after 3 h and over 90% for WF-2 and 85% for WF-6 after 5 h. The remaining five strains showed relatively lower auto-aggregation rates, ranging from 30% to 55% at 5 h. These results indicate that all seven strains have the potential to adhere to host intestinal epithelial cell surface.

The MATH assay showed that WF-1, WF-2, WF-5, WF-7 had high levels of cell surface hydrophobicity (over 97%) followed by WF-4 (over 85%). WF-6 showed about 40% hydrophobicity and WF-3 was totally hydrophilic. These results indicate that, except for WF-3, all other strains have the potential to adhere to host intestinal epithelial cell surface.

The low pH change study showed that six strains (except WF-6) survived in a solution (pH=2.0, 2.5 or 3.0) for 6 h, and WF-6 survived for 2 h in a solution with pH=2.0 or 2.5, and for 6 h when pH=3.0. Overall, WF-1 was the most acid tolerant strain, followed by WF-4, WF-7, WF-3, WF-2, WF-5. The least acid tolerant strain was WF-6.

The bile salt tolerance assay showed that all seven strains were bile salt tolerant. All strains could tolerate 5% bile salt for 24 h. WF-2 and WF-6 showed relatively lower tolerance to bile salt compared to the other five strains.

The gastric digestive enzyme tolerance assay showed that five strains (except for WF-2 and WF-3) survived in a Simulated Gastric Fluid (SGF, with 3.2 mg/mL of pepsin) at pH 2.0 for 2h. All strains survived in an SGF solution at pH 2.5 (except WF-2 and WF-6) or 3.0 for 6 h. WF-2 and WF-6 survived in an SGF solution at pH 2.5 for 4 h.

All seven strains survived in a Simulated Intestinal Fluid (SIF) with 10 mg/mL of pancreatin, an intestinal digestive enzyme, for 24 h. Moreover, all seven strains showed an increase in viable cell count, instead of a decrease, over time.

All seven strains produced inhibitory substances against at 10 out of 14 indicator strains tested in this study.

According to the MIC cut-off values suggested by the EFSA (European Food Safety Authority), all seven strains were resistant to at least 1 out of 8 antibiotics tested in this study.

The cell binding assay showed that all seven strains could bind to canine-originated cell lines, MDCK and DH82, which indicate that all seven strains have the capability to adhere to canine intestinal epithelial cell surfaces and colonize in the intestine. WF-5 showed the highest cell surface binding capability.

The cytokine gene expression assays in canine originated cells lines, MDCK and DH82, showed that DH82 was a better cell model for immunomodulation compared to MDCK. All seven strains had the capability to modulate the expression of certain cytokines.

All seven strains were successfully fermented in MRS broth and freeze-dried in-house, followed by storage at three different temperatures, 4° C., 25° C., and 37° C. Six strains were stable in terms of viable cell count at 4° C. for up to 16 weeks, and it was 10 weeks for WF-6. The most stable strain was WF-3, followed by WF-5, WF-7, WF-1, and WF-4. The least stable strain was WF-6.

All seven strains in the format of freeze-dried powder were incorporated into a commercial raw frozen meat diet, and all strains survived and remained stable in the course of the recommended length of shelf life, that is, to finish the product within two days once it is thawed and refrigerated.

Various modifications besides those already described are possible without departing from the concepts disclosed herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Use of broader terms such as comprises, includes, having, etc. should be understood to provide support for narrower terms such as consisting of, consisting essentially of, comprised substantially of, etc.

Although particular embodiments have been shown and described, it will be appreciated by those skilled in the art that various changes and modifications might be made without departing from the scope of the disclosure. The terms and expressions used in the preceding specification have been used herein as terms of description and not of limitation, and there is no intention in the use of such terms and expressions of excluding equivalents of the features shown and described or portions thereof.

The invention claimed is:

1. An isolated strain of gastrointestinal bacteria isolated from feces of a free ranging wolf for use as a probiotic in a subject, wherein the subject is a domestic dog and the isolated strain is capable of binding canine cells, wherein the isolated strain is in lyophilized form; and wherein the isolated strain is selected from *Lactobacillus reuteri* strain WF-1 IDAC Accession number 181218-01; *Lactobacillus animalis* strain WF-2 IDAC Accession number 181218-02; *Enterococcus faecium* strain WF-3 IDAC Accession number 181218-03; *Lactobacillus plantarum* strain WF-4 IDAC Accession number 181218-04; *Lactobacillus brevis* strain WF-5 IDAC Accession number 181218-05; *Lactobacillus curvatus* strain WF-6 IDAC Accession number 181218-06; and *Lactobacillus reuteri* strain WF-7 IDAC Accession number 181218-07.

2. A composition comprising at least one isolated strain of wolf probiotic bacteria isolated from feces of a free ranging wolf wherein the at least one isolated strain is capable of binding canine cells, wherein the at least one isolated strain in in lyophilized form; and wherein the at least one isolated strain is selected from *Lactobacillus reuteri* strain WF-1 IDAC Accession number 181218-01; *Lactobacillus animalis* strain WF-2 IDAC Accession number 181218-02; *Enterococcus faecium* strain WF-3 IDAC Accession number 181218-03; *Lactobacillus plantarum* strain WF-4 IDAC Accession number 181218-04; *Lactobacillus brevis* strain WF-5 IDAC Accession number 181218-05; *Lactobacillus curvatus* strain WF-6 IDAC Accession number 181218-06; and *Lactobacillus reuteri* strain WF-7 IDAC Accession number 181218-07.

3. The composition of claim 2, further comprising one or more of a prebiotic, an additional pharmaceutical or nutritional ingredient, or a pharmaceutically or nutritionally acceptable excipient.

4. The composition of claim 2, wherein the composition is in the form of a dietary supplement.

5. The composition of claim 2, wherein the composition is in the form of a food product.

6. The composition of claim 5, wherein the food product comprises a dog food or a dog treat.

7. The isolated strain of claim 1, wherein the free ranging wolf is native to Prince Albert National Park, Saskatchewan, Canada.

8. The composition of claim 2, wherein the free ranging wolf is native to Prince Albert National Park, Saskatchewan, Canada.

9. The composition of claim 2, wherein the composition comprises two or more isolated strains of the at least one isolated strain of wolf probiotic bacteria.

10. The composition of claim 4, wherein the dietary supplement is in the form of a powder, a capsule, a gel capsule, a microcapsule, a bead, a tablet, a chewable tablet, a gummy, or a liquid.

11. The composition of claim 5, wherein the food product is a solid food product.

12. The composition of claim 5, wherein the food product is a liquid food product.

13. The composition of claim 5, wherein the composition is in the form of a surface coating on a solid food product.

\* \* \* \* \*